(12) United States Patent
Palmaz

(10) Patent No.: US 12,351,792 B2
(45) Date of Patent: *Jul. 8, 2025

(54) SYSTEM AND METHOD FOR MONITORING AND CONTROLLING CONDITIONS WITHIN A VESSEL

(71) Applicant: Cedar Knoll Vineyard, Inc., Napa, CA (US)

(72) Inventor: Christian G. Palmaz, Napa, CA (US)

(73) Assignee: Cedar Knoll Vineyards, Inc., Napa, CA (US)

( * ) Notice: Subject to any disclaimer, the term of this patent is extended or adjusted under 35 U.S.C. 154(b) by 135 days.

This patent is subject to a terminal disclaimer.

(21) Appl. No.: 18/329,219

(22) Filed: Jun. 5, 2023

(65) Prior Publication Data

US 2024/0043785 A1    Feb. 8, 2024

Related U.S. Application Data

(63) Continuation of application No. 16/545,492, filed on Aug. 20, 2019, now Pat. No. 11,702,624.

(Continued)

(51) Int. Cl.
     *C12G 1/02*           (2006.01)
     *C12G 1/028*          (2006.01)
     (Continued)

(52) U.S. Cl.
     CPC ........... *C12M 41/48* (2013.01); *C12G 1/0213* (2013.01); *C12M 23/42* (2013.01); *C12M 41/12* (2013.01);
     (Continued)

(58) Field of Classification Search
     CPC ...... C12M 41/48; C12M 23/42; C12M 41/12; C12M 41/18; C12M 41/26; C12M 41/32; C12M 41/34; C12M 41/40; C12G 1/0213; G01K 1/026; G01K 2213/00
     USPC ......... 374/110, 111, 112, 115, 137; 210/614, 210/739, 740, 742, 743, 745, 746, 175; 426/11
     See application file for complete search history.

(56) References Cited

U.S. PATENT DOCUMENTS

| | | |
|---|---|---|
| 4,322,297 A | 3/1982 | Bajka |
| 4,711,785 A | 12/1987 | Bruch |
| | (Continued) | |

FOREIGN PATENT DOCUMENTS

| | | |
|---|---|---|
| CN | 2480370 | 3/2002 |
| DE | 10131158 A1 | 1/2003 |
| | (Continued) | |

OTHER PUBLICATIONS

Machine-generated English translation of JP 2015509443, generated on Dec. 12, 2024.*

(Continued)

*Primary Examiner* — Fred Prince
(74) *Attorney, Agent, or Firm* — Rosenbaum IP, P.C.; David G. Rosenbaum

(57) ABSTRACT

A system and method for regression modeling an interior volume of a containment vessel and interpolating data from multi-point sensor arrays within the containment vessel to detect conditions across the interior volume of the containment vessel.

20 Claims, 71 Drawing Sheets
(39 of 71 Drawing Sheet(s) Filed in Color)

Related U.S. Application Data

(60) Provisional application No. 62/724,288, filed on Aug. 29, 2018.

(51) Int. Cl.
*C12M 1/02* (2006.01)
*C12M 1/34* (2006.01)
*C12M 1/36* (2006.01)
*C12M 3/00* (2006.01)
*G01K 1/02* (2021.01)

(52) U.S. Cl.
CPC ............ *C12M 41/18* (2013.01); *C12M 41/26* (2013.01); *C12M 41/32* (2013.01); *C12M 41/34* (2013.01); *C12M 41/40* (2013.01); *G01K 1/026* (2013.01); *G01K 2213/00* (2013.01)

(56) References Cited

U.S. PATENT DOCUMENTS

| | | | |
|---|---|---|---|
| 4,856,421 A | 8/1989 | Whitford | |
| 7,004,625 B2 | 2/2006 | Egidio | |
| 8,794,049 B1 | 8/2014 | Norkin et al. | |
| 2003/0116487 A1 | 6/2003 | Petersen | |
| 2003/0217975 A1 | 11/2003 | Yu et al. | |
| 2003/0219062 A1 | 11/2003 | Egidio | |
| 2005/0077029 A1 | 4/2005 | Cervantes et al. | |
| 2016/0109345 A1 | 4/2016 | Kravitz | |

FOREIGN PATENT DOCUMENTS

| | | |
|---|---|---|
| DE | 10247654 A1 | 1/2003 |
| EP | 0253546 A2 | 1/1988 |
| FR | 2743145 | 4/1997 |
| JP | 2015509443 A * | 3/2015 |

OTHER PUBLICATIONS

Lekien, F., et al., Tricubic interpolation in three dimensions, Int. J. Numer. Meth. Engng., 2005; 63: pp. 455-471.

Notification of Transmittal of the International Search Report and The Written Opinion of the International Searching Authority, or the Declaration. Foreign Application No. PCT/US019/047478 (Dec. 13, 2019).

The Written Opinion of the International Searching Authority. Foreign Application No. PCT/US019/047478 (Dec. 13, 2019).

* cited by examiner

| Position Number (in.) | Outer Longitudinal Cubic-Ref Number | Inner Logitudinal Cubic-Ref Number | Latitudinal Cubic-Ref Number |
|---|---|---|---|
| 1 | | | -0.35 |
| 2 | | | -0.42 |
| 3 | | | -0.49 |
| 4 | | | -0.55 |
| 5 | | | -0.62 |
| 6 | | | -0.69 |
| 7 | | | -0.75 |
| 8 | 0.13 | -1.75 | -0.82 |
| 9 | | | -0.89 |
| 10 | | | -0.96 |
| 11 | | | -1.02 |
| 12 | | | -1.09 |
| 13 | | | -1.16 |
| 14 | | | -1.22 |
| 15 | | | -1.29 |
| 16 | -0.38 | -0.13 | -1.36 |
| 17 | | | -1.35 |
| 18 | | | -1.34 |
| 19 | | | -1.33 |
| 20 | | | -1.32 |
| 21 | | | -1.31 |
| 22 | | | -1.30 |

FIG. 6(Cont.)

| 1 | 2 | 3 | 4 |
| --- | --- | --- | --- |
| 74.11 | 74.46 | 74.82 | 75.17 |
| 73.65 | 74.07 | 74.49 | 74.91 |
| 73.19 | 73.68 | 74.17 | 74.65 |
| 72.73 | 73.29 | 73.84 | 74.39 |
| 72.27 | 72.89 | 73.51 | 74.13 |
| 71.81 | 72.50 | 73.19 | 73.88 |
| 71.35 | 72.11 | 72.86 | 73.62 |
| 70.89 | 71.71 | 72.54 | 73.36 |
| 70.43 | 71.32 | 72.21 | 73.10 |
| 69.97 | 70.93 | 71.88 | 72.84 |
| 69.51 | 70.54 | 71.56 | 72.58 |
| 69.05 | 70.14 | 71.23 | 72.32 |
| 68.59 | 69.75 | 70.91 | 72.06 |
| 68.13 | 69.36 | 70.58 | 71.80 |
| 67.67 | 68.96 | 70.25 | 71.54 |
| 67.21 | 68.57 | 69.93 | 71.29 |
| 67.63 | 68.98 | 70.33 | 71.68 |
| 68.05 | 69.39 | 70.73 | 72.07 |
| 68.47 | 69.80 | 71.13 | 72.46 |
| 68.89 | 70.21 | 71.54 | 72.86 |
| 69.31 | 70.63 | 71.94 | 73.25 |
| 69.73 | 71.04 | 72.34 | 73.64 |

FIG. 6(Cont.)

| 5 | 6 - Outer value | 7 | 8 |
|---|---|---|---|
| 75.52 | 75.88 | 76.23 | 76.58 |
| 75.33 | 75.75 | 76.17 | 76.59 |
| 75.14 | 75.63 | 76.11 | 76.60 |
| 74.95 | 75.50 | 76.05 | 76.61 |
| 74.75 | 75.38 | 76.00 | 76.62 |
| 74.56 | 75.25 | 75.94 | 76.63 |
| 74.37 | 75.13 | 75.88 | 76.63 |
| 74.18 | 75.00 | 75.82 | 76.64 |
| 73.99 | 74.88 | 75.76 | 76.65 |
| 73.79 | 74.75 | 75.71 | 76.66 |
| 73.60 | 74.63 | 75.65 | 76.67 |
| 73.41 | 74.50 | 75.59 | 76.68 |
| 73.22 | 74.38 | 75.53 | 76.69 |
| 73.03 | 74.25 | 75.47 | 76.70 |
| 72.83 | 74.13 | 75.42 | 76.71 |
| 72.64 | 74.00 | 75.36 | 76.71 |
| 73.03 | 74.38 | 75.72 | 77.07 |
| 73.41 | 74.75 | 76.09 | 77.43 |
| 73.79 | 75.13 | 76.46 | 77.79 |
| 74.18 | 75.50 | 76.82 | 78.14 |
| 74.56 | 75.88 | 77.19 | 78.50 |
| 74.95 | 76.25 | 77.55 | 78.86 |

FIG. 6(Cont.)

| 9 | 10 | 11 | 12 |
|---|---|---|---|
| 76.93 | 77.29 | 77.64 | 77.99 |
| 77.01 | 77.43 | 77.85 | 78.27 |
| 77.08 | 77.57 | 78.06 | 78.54 |
| 77.16 | 77.71 | 78.27 | 78.82 |
| 77.24 | 77.86 | 78.48 | 79.10 |
| 77.31 | 78.00 | 78.69 | 79.38 |
| 77.39 | 78.14 | 78.90 | 79.65 |
| 77.46 | 78.29 | 79.11 | 79.93 |
| 77.54 | 78.43 | 79.32 | 80.21 |
| 77.62 | 78.57 | 79.53 | 80.48 |
| 77.69 | 78.71 | 79.74 | 80.76 |
| 77.77 | 78.86 | 79.95 | 81.04 |
| 77.84 | 79.00 | 80.16 | 81.31 |
| 77.92 | 79.14 | 80.37 | 81.59 |
| 78.00 | 79.29 | 80.58 | 81.87 |
| 78.07 | 79.43 | 80.79 | 82.14 |
| 78.42 | 79.77 | 81.12 | 82.46 |
| 78.77 | 80.11 | 81.45 | 82.79 |
| 79.12 | 80.45 | 81.78 | 83.11 |
| 79.46 | 80.79 | 82.11 | 83.43 |
| 79.81 | 81.13 | 82.44 | 83.75 |
| 80.16 | 81.46 | 82.77 | 84.07 |

FIG. 6(Cont.)

| 13 | 14 | 15 | 16 |
| --- | --- | --- | --- |
| 78.34 | 78.70 | 79.05 | 79.40 |
| 78.69 | 79.11 | 79.53 | 79.95 |
| 79.03 | 79.52 | 80.00 | 80.49 |
| 79.38 | 79.93 | 80.48 | 81.04 |
| 79.72 | 80.34 | 80.96 | 81.58 |
| 80.06 | 80.75 | 81.44 | 82.13 |
| 80.41 | 81.16 | 81.92 | 82.67 |
| 80.75 | 81.57 | 82.39 | 83.21 |
| 81.09 | 81.98 | 82.87 | 83.76 |
| 81.44 | 82.39 | 83.35 | 84.30 |
| 81.78 | 82.80 | 83.83 | 84.85 |
| 82.13 | 83.21 | 84.30 | 85.39 |
| 82.47 | 83.63 | 84.78 | 85.94 |
| 82.81 | 84.04 | 85.26 | 86.48 |
| 83.16 | 84.45 | 85.74 | 87.03 |
| 83.50 | 84.86 | 86.21 | 87.57 |
| 83.81 | 85.16 | 86.51 | 87.86 |
| 84.13 | 85.46 | 86.80 | 88.14 |
| 84.44 | 85.77 | 87.10 | 88.43 |
| 84.75 | 86.07 | 87.39 | 88.71 |
| 85.06 | 86.38 | 87.69 | 89.00 |
| 85.38 | 86.68 | 87.98 | 89.29 |

FIG. 6(Cont.)

| 17 | 18 | 19 | 20 |
|---|---|---|---|
| 79.75 | 80.11 | 80.46 | 80.81 |
| 80.37 | 81.79 | 81.21 | 81.63 |
| 80.98 | 81.46 | 81.95 | 82.44 |
| 81.59 | 82.14 | 82.70 | 83.25 |
| 82.20 | 82.82 | 83.44 | 84.06 |
| 82.81 | 83.50 | 84.19 | 84.88 |
| 83.42 | 84.18 | 84.93 | 85.69 |
| 84.04 | 84.86 | 85.68 | 86.50 |
| 84.65 | 85.54 | 86.42 | 87.31 |
| 85.26 | 86.21 | 87.17 | 88.12 |
| 85.87 | 86.89 | 87.92 | 88.94 |
| 86.48 | 87.57 | 88.66 | 89.75 |
| 87.09 | 88.25 | 89.41 | 90.56 |
| 87.71 | 88.93 | 90.15 | 91.38 |
| 88.32 | 89.61 | 90.90 | 92.19 |
| 88.93 | 90.29 | 91.64 | 93.00 |
| 89.21 | 90.55 | 91.90 | 93.25 |
| 89.48 | 90.82 | 92.16 | 93.50 |
| 89.76 | 91.09 | 92.42 | 93.75 |
| 90.04 | 91.36 | 92.68 | 94.00 |
| 90.31 | 91.63 | 92.94 | 94.25 |
| 90.59 | 91.89 | 93.20 | 94.50 |

FIG. 6(Cont.)

| 21 | 22 | 23 | 24 | 25 |
|---|---|---|---|---|
| 81.17 | 81.52 | 81.87 | 82.22 | 82.58 |
| 82.04 | 82.46 | 82.88 | 83.30 | 83.72 |
| 82.92 | 83.41 | 83.90 | 84.38 | 84.87 |
| 83.80 | 84.36 | 84.91 | 85.46 | 86.02 |
| 84.68 | 85.30 | 85.92 | 86.54 | 87.17 |
| 85.56 | 86.25 | 86.94 | 87.63 | 88.31 |
| 86.44 | 87.20 | 87.95 | 88.71 | 89.46 |
| 87.32 | 88.14 | 88.96 | 89.79 | 90.61 |
| 88.20 | 89.09 | 89.98 | 90.87 | 91.75 |
| 89.08 | 90.04 | 90.99 | 91.95 | 92.90 |
| 89.96 | 90.98 | 92.00 | 93.03 | 94.05 |
| 90.84 | 91.93 | 93.02 | 94.11 | 95.20 |
| 91.72 | 92.88 | 94.03 | 95.19 | 96.34 |
| 92.60 | 93.82 | 95.04 | 96.27 | 97.49 |
| 93.48 | 94.77 | 96.06 | 97.35 | 98.64 |
| 94.36 | 95.71 | 97.07 | 98.43 | 99.79 |
| 94.60 | 95.95 | 97.29 | 98.64 | 99.99 |
| 94.84 | 96.18 | 97.52 | 98.86 | 100.20 |
| 95.08 | 96.41 | 97.74 | 99.07 | 100.40 |
| 95.32 | 96.64 | 97.96 | 99.29 | 100.61 |
| 95.56 | 96.88 | 98.19 | 99.50 | 100.81 |
| 95.80 | 97.11 | 98.41 | 99.71 | 101.02 |

FIG. 6(Cont.)

| 26 | 27 | 28 | 29 | 30 |
|---|---|---|---|---|
| 83.93 | 83.28 | 83.63 | 83.99 | 84.34 |
| 84.14 | 84.56 | 84.98 | 85.40 | 85.82 |
| 85.36 | 85.84 | 86.33 | 86.82 | 87.30 |
| 86.57 | 87.13 | 87.68 | 88.23 | 88.79 |
| 87.79 | 88.41 | 89.03 | 89.65 | 90.27 |
| 89.00 | 89.69 | 90.38 | 91.06 | 91.75 |
| 90.21 | 90.97 | 91.72 | 92.48 | 93.23 |
| 91.43 | 92.25 | 93.07 | 93.89 | 94.71 |
| 92.64 | 93.53 | 94.42 | 95.31 | 96.20 |
| 93.86 | 94.81 | 95.77 | 96.72 | 97.68 |
| 95.07 | 96.09 | 97.12 | 98.14 | 99.16 |
| 96.29 | 97.37 | 98.46 | 99.55 | 100.64 |
| 97.50 | 98.66 | 99.81 | 100.97 | 102.13 |
| 98.71 | 99.94 | 101.16 | 102.38 | 103.61 |
| 99.93 | 101.22 | 102.51 | 103.80 | 105.09 |
| 101.14 | 102.50 | 103.86 | 105.21 | 106.57 |
| 101.34 | 102.69 | 104.04 | 105.38 | 106.73 |
| 101.54 | 102.88 | 104.21 | 105.55 | 106.89 |
| 101.73 | 103.06 | 104.39 | 105.72 | 107.05 |
| 101.93 | 103.25 | 104.57 | 105.89 | 107.21 |
| 102.13 | 103.44 | 104.75 | 106.06 | 107.38 |
| 102.32 | 103.63 | 104.93 | 106.23 | 107.54 |

FIG. 6(Cont.)

| 31 | 32 | 33 | 34 - Center Value |
|---|---|---|---|
| 85.69 | 85.04 | 85.40 | 85.75 |
| 86.24 | 86.66 | 87.08 | 87.50 |
| 87.79 | 88.28 | 88.76 | 89.25 |
| 89.34 | 89.89 | 90.45 | 91.00 |
| 90.89 | 91.51 | 92.13 | 92.75 |
| 92.44 | 93.13 | 93.81 | 94.50 |
| 93.99 | 94.74 | 95.50 | 96.25 |
| 95.54 | 96.36 | 97.18 | 98.00 |
| 97.08 | 97.97 | 98.86 | 99.75 |
| 98.63 | 99.59 | 100.54 | 101.50 |
| 100.18 | 101.21 | 102.23 | 103.25 |
| 101.73 | 102.82 | 103.91 | 105.00 |
| 103.28 | 104.44 | 105.59 | 106.75 |
| 104.83 | 106.05 | 107.28 | 108.50 |
| 106.38 | 107.67 | 108.96 | 110.25 |
| 107.93 | 109.29 | 110.64 | 112.00 |
| 108.08 | 109.43 | 110.78 | 112.13 |
| 108.23 | 109.57 | 110.91 | 112.25 |
| 108.38 | 109.71 | 111.04 | 112.38 |
| 108.54 | 109.86 | 111.18 | 112.50 |
| 108.69 | 110.00 | 111.31 | 112.63 |
| 108.84 | 110.14 | 111.45 | 112.75 |

FIG. 6(Cont.)

| | | | |
|---|---|---|---|
| 23 | | | -1.29 |
| 24 | -0.13 | 1.88 | -1.29 |
| 25 | | | -1.21 |
| 26 | | | -1.14 |
| 27 | | | -1.07 |
| 28 | | | -1.00 |
| 29 | | | -0.93 |
| 30 | | | -0.86 |
| 31 | | | -0.72 |
| 32 | 1.63 | 1.13 | -0.71 |
| 33 | | | -0.73 |
| 34 | | | -0.75 |
| 35 | | | -0.77 |
| 36 | | | -0.79 |
| 37 | | | -0.80 |
| 38 | | | -0.82 |
| 39 | | | -0.84 |
| 40 | 0.75 | 1.63 | -0.86 |
| 41 | | | -0.83 |
| 42 | | | -0.79 |
| 43 | | | -0.76 |
| 44 | | | -0.73 |

FIG. 6(Cont.)

| | | | |
|---|---|---|---|
| 70.15 | 71.45 | 72.74 | 74.04 |
| 70.57 | 71.86 | 73.14 | 74.43 |
| 71.05 | 72.27 | 73.48 | 74.70 |
| 71.54 | 72.68 | 73.82 | 74.96 |
| 72.02 | 73.09 | 74.16 | 75.23 |
| 72.50 | 73.50 | 74.50 | 75.50 |
| 72.98 | 73.91 | 74.84 | 75.77 |
| 73.46 | 74.32 | 75.18 | 76.04 |
| 74.28 | 75.00 | 75.72 | 76.44 |
| 74.43 | 75.14 | 75.86 | 76.57 |
| 72.71 | 73.45 | 74.18 | 74.91 |
| 71.00 | 71.75 | 72.50 | 73.25 |
| 69.29 | 70.05 | 70.82 | 71.59 |
| 67.57 | 68.36 | 69.14 | 69.93 |
| 65.86 | 66.66 | 67.46 | 68.27 |
| 64.14 | 64.96 | 65.79 | 66.61 |
| 62.43 | 63.27 | 64.11 | 64.95 |
| 60.71 | 61.57 | 62.43 | 63.29 |
| 60.12 | 60.95 | 61.77 | 62.60 |
| 59.53 | 60.32 | 61.12 | 61.91 |
| 58.93 | 59.70 | 60.46 | 61.22 |
| 58.34 | 59.07 | 59.80 | 60.54 |

FIG. 6(Cont.)

| | | | |
|---|---|---|---|
| 75.33 | 76.63 | 77.92 | 79.21 |
| 75.71 | 77.00 | 78.29 | 79.57 |
| 75.91 | 77.13 | 78.34 | 79.55 |
| 76.11 | 77.25 | 78.39 | 79.54 |
| 76.30 | 77.38 | 78.45 | 79.52 |
| 76.50 | 77.50 | 78.50 | 79.50 |
| 76.70 | 77.63 | 78.55 | 79.48 |
| 76.89 | 77.75 | 78.61 | 79.46 |
| 77.16 | 77.88 | 78.59 | 79.31 |
| 77.29 | 78.00 | 78.71 | 79.43 |
| 75.64 | 76.38 | 77.11 | 77.84 |
| 74.00 | 74.75 | 75.50 | 76.25 |
| 72.36 | 73.13 | 73.89 | 74.66 |
| 70.71 | 71.50 | 72.29 | 73.07 |
| 69.07 | 69.88 | 70.68 | 71.48 |
| 67.43 | 68.25 | 69.07 | 69.89 |
| 65.79 | 66.63 | 67.46 | 68.30 |
| 64.14 | 65.00 | 65.86 | 66.71 |
| 63.42 | 64.25 | 65.08 | 65.90 |
| 62.71 | 63.50 | 64.29 | 65.09 |
| 61.99 | 62.75 | 63.51 | 64.28 |
| 61.27 | 62.00 | 62.73 | 63.46 |

FIG. 6(Cont.)

| | | | |
|---|---|---|---|
| 80.51 | 81.80 | 83.10 | 84.39 |
| 80.86 | 82.14 | 83.43 | 84.71 |
| 80.77 | 81.98 | 83.20 | 84.41 |
| 80.68 | 81.82 | 82.96 | 84.11 |
| 80.59 | 81.66 | 82.73 | 83.80 |
| 80.50 | 81.50 | 82.50 | 83.50 |
| 80.41 | 81.34 | 82.27 | 83.20 |
| 80.32 | 81.18 | 82.04 | 82.89 |
| 80.03 | 80.75 | 81.47 | 82.19 |
| 80.14 | 80.86 | 81.57 | 82.29 |
| 78.57 | 79.30 | 80.04 | 80.77 |
| 77.00 | 77.75 | 78.50 | 79.25 |
| 75.43 | 76.20 | 76.96 | 77.73 |
| 73.86 | 74.64 | 75.43 | 76.21 |
| 72.29 | 73.09 | 73.89 | 74.70 |
| 70.71 | 71.54 | 72.36 | 73.18 |
| 69.14 | 69.98 | 70.82 | 71.66 |
| 67.57 | 68.43 | 69.29 | 70.14 |
| 66.73 | 67.55 | 68.38 | 69.21 |
| 65.88 | 66.68 | 67.47 | 68.27 |
| 65.04 | 65.80 | 66.57 | 67.33 |
| 64.20 | 64.93 | 65.66 | 66.39 |

FIG. 6(Cont.)

| | | | |
|---|---|---|---|
| 85.69 | 86.98 | 88.28 | 89.57 |
| 86.00 | 87.29 | 88.57 | 89.86 |
| 85.63 | 86.84 | 88.05 | 89.27 |
| 85.25 | 86.39 | 87.54 | 88.68 |
| 84.88 | 85.95 | 87.02 | 88.09 |
| 84.50 | 85.50 | 86.50 | 87.50 |
| 84.13 | 85.05 | 85.98 | 86.91 |
| 83.75 | 84.61 | 85.46 | 86.32 |
| 82.91 | 83.63 | 84.34 | 85.06 |
| 83.00 | 83.71 | 84.43 | 85.14 |
| 81.50 | 82.23 | 82.96 | 83.70 |
| 80.00 | 80.75 | 81.50 | 82.25 |
| 78.50 | 79.27 | 80.04 | 80.80 |
| 77.00 | 77.79 | 78.57 | 79.36 |
| 75.50 | 76.30 | 77.11 | 77.91 |
| 74.00 | 74.82 | 75.64 | 76.46 |
| 72.50 | 73.34 | 74.18 | 75.02 |
| 71.00 | 71.86 | 72.71 | 73.57 |
| 70.03 | 70.86 | 71.68 | 72.51 |
| 69.06 | 69.86 | 70.65 | 71.45 |
| 68.09 | 68.86 | 69.62 | 70.38 |
| 67.13 | 67.86 | 68.59 | 69.32 |

FIG. 6(Cont.)

| | | | |
|---|---|---|---|
| 90.87 | 92.16 | 93.46 | 94.75 |
| 91.14 | 92.43 | 93.71 | 95.00 |
| 90.48 | 91.70 | 92.91 | 94.12 |
| 89.82 | 90.96 | 92.11 | 93.25 |
| 89.16 | 90.23 | 91.30 | 92.38 |
| 88.50 | 89.50 | 90.50 | 91.50 |
| 87.84 | 88.77 | 89.70 | 90.63 |
| 87.18 | 88.04 | 88.89 | 89.75 |
| 85.78 | 86.50 | 87.22 | 87.94 |
| 85.86 | 86.57 | 87.29 | 88.00 |
| 84.43 | 85.16 | 85.89 | 86.63 |
| 83.00 | 83.75 | 84.50 | 85.25 |
| 81.57 | 82.34 | 83.11 | 83.87 |
| 80.14 | 80.93 | 81.71 | 82.50 |
| 78.71 | 79.52 | 80.32 | 81.13 |
| 77.29 | 78.11 | 78.93 | 79.75 |
| 75.86 | 76.70 | 77.54 | 78.37 |
| 74.43 | 75.29 | 76.14 | 77.00 |
| 73.33 | 74.16 | 74.99 | 75.81 |
| 72.24 | 73.04 | 73.83 | 74.63 |
| 71.15 | 71.91 | 72.67 | 73.44 |
| 70.05 | 70.79 | 71.52 | 72.25 |

FIG. 6(Cont.)

| | | | | |
|---|---|---|---|---|
| 96.04 | 97.34 | 98.63 | 99.93 | 101.22 |
| 96.29 | 97.57 | 98.86 | 100.14 | 101.43 |
| 95.34 | 96.55 | 97.77 | 98.98 | 100.20 |
| 94.39 | 95.54 | 96.68 | 97.82 | 98.96 |
| 93.45 | 94.52 | 95.59 | 96.66 | 97.73 |
| 92.50 | 93.50 | 94.50 | 95.50 | 96.50 |
| 91.55 | 92.48 | 93.41 | 94.34 | 95.27 |
| 90.61 | 91.46 | 92.32 | 93.18 | 94.04 |
| 88.66 | 89.38 | 90.09 | 90.81 | 91.53 |
| 88.71 | 89.43 | 90.14 | 90.86 | 91.57 |
| 87.36 | 88.09 | 88.82 | 89.55 | 90.29 |
| 86.00 | 86.75 | 87.50 | 88.25 | 89.00 |
| 84.64 | 85.41 | 86.18 | 86.95 | 87.71 |
| 83.29 | 84.07 | 84.86 | 85.64 | 86.43 |
| 81.93 | 82.73 | 83.54 | 84.34 | 85.14 |
| 80.57 | 81.39 | 82.21 | 83.04 | 83.86 |
| 79.21 | 80.05 | 80.89 | 81.73 | 82.57 |
| 77.86 | 78.71 | 79.57 | 80.43 | 81.29 |
| 76.64 | 77.46 | 78.29 | 79.12 | 79.94 |
| 75.42 | 76.21 | 77.01 | 77.80 | 78.60 |
| 74.20 | 74.96 | 75.73 | 76.49 | 77.25 |
| 72.98 | 73.71 | 74.45 | 75.18 | 75.91 |

FIG. 6(Cont.)

| 102.52 | 103.81 | 105.11 | 106.40 | 107.70 |
| --- | --- | --- | --- | --- |
| 102.71 | 104.00 | 105.29 | 106.57 | 107.86 |
| 101.41 | 102.63 | 103.84 | 105.05 | 106.27 |
| 100.11 | 101.25 | 102.39 | 103.54 | 104.68 |
| 98.80 | 99.88 | 100.95 | 102.02 | 103.09 |
| 97.50 | 98.50 | 99.50 | 100.50 | 101.50 |
| 96.20 | 97.13 | 98.05 | 98.98 | 99.91 |
| 94.89 | 95.75 | 96.61 | 97.46 | 98.32 |
| 92.25 | 92.97 | 93.69 | 94.41 | 95.13 |
| 92.29 | 93.00 | 93.71 | 94.43 | 95.14 |
| 91.02 | 91.75 | 92.48 | 93.21 | 93.95 |
| 89.75 | 90.50 | 91.25 | 92.00 | 92.75 |
| 88.48 | 89.25 | 90.02 | 90.79 | 91.55 |
| 87.21 | 88.00 | 88.79 | 89.57 | 90.36 |
| 85.95 | 86.75 | 87.55 | 88.36 | 89.16 |
| 84.68 | 85.50 | 86.32 | 87.14 | 87.96 |
| 83.41 | 84.25 | 85.09 | 85.93 | 86.77 |
| 82.14 | 83.00 | 83.86 | 84.71 | 85.57 |
| 80.77 | 81.59 | 82.42 | 83.25 | 84.07 |
| 79.39 | 80.19 | 80.98 | 81.78 | 82.57 |
| 78.02 | 78.78 | 79.54 | 80.31 | 81.07 |
| 76.64 | 77.38 | 78.11 | 78.84 | 79.57 |

FIG. 6(Cont.)

| | | | |
|---|---|---|---|
| 108.99 | 110.29 | 111.58 | 112.88 |
| 109.14 | 110.43 | 111.71 | 113.00 |
| 107.48 | 108.70 | 109.91 | 111.13 |
| 105.82 | 106.96 | 108.11 | 109.25 |
| 104.16 | 105.23 | 106.30 | 107.38 |
| 102.50 | 103.50 | 104.50 | 105.50 |
| 100.84 | 101.77 | 102.70 | 103.63 |
| 99.18 | 100.04 | 100.89 | 101.75 |
| 95.84 | 96.56 | 97.28 | 99.88 |
| 95.86 | 96.57 | 97.29 | 98.00 |
| 94.68 | 95.41 | 96.14 | 96.88 |
| 93.50 | 94.25 | 95.00 | 95.75 |
| 92.32 | 93.09 | 93.86 | 94.63 |
| 91.14 | 91.93 | 92.71 | 93.50 |
| 89.96 | 90.77 | 91.57 | 92.38 |
| 88.79 | 89.61 | 90.43 | 91.25 |
| 87.61 | 88.45 | 89.29 | 90.13 |
| 86.43 | 87.29 | 88.14 | 89.00 |
| 84.90 | 85.72 | 86.55 | 87.38 |
| 83.37 | 84.16 | 84.96 | 85.75 |
| 81.83 | 82.60 | 83.36 | 84.13 |
| 80.30 | 81.04 | 81.77 | 82.50 |

FIG. 6(Cont.)

| | | | |
|---|---|---|---|
| 45 | | | -0.70 |
| 46 | | | -0.67 |
| 47 | | | -0.64 |
| 48 | 0.38 | 0.13 | -0.61 |
| 49 | | | -0.62 |
| 50 | | | -0.63 |
| 51 | | | -0.63 |
| 52 | | | -0.64 |
| 53 | | | -0.65 |
| 54 | | | -0.66 |
| 55 | | | -0.67 |
| 56 | 0.38 | 0.88 | -0.68 |
| 57 | | | -0.66 |
| 58 | | | -0.64 |
| 59 | | | -0.63 |
| 60 | | | -0.61 |
| 61 | | | -0.59 |
| 62 | | | -0.57 |
| 63 | | | -0.55 |
| 64 | | | -0.54 |
| 65 | | | -0.55 |
| 66 | | | -0.57 |
| 67 | | | -0.59 |

FIG. 6(Cont.)

| | | | |
|---|---|---|---|
| 57.75 | 58.45 | 59.15 | 59.85 |
| 57.15 | 57.82 | 58.49 | 59.16 |
| 56.56 | 57.20 | 57.83 | 58.47 |
| 55.96 | 56.57 | 57.18 | 57.79 |
| 55.54 | 56.16 | 56.78 | 57.39 |
| 55.13 | 55.75 | 56.38 | 57.00 |
| 54.71 | 55.34 | 55.97 | 56.61 |
| 54.29 | 54.93 | 55.57 | 56.21 |
| 53.87 | 54.52 | 55.17 | 55.82 |
| 53.45 | 54.11 | 54.77 | 55.43 |
| 53.03 | 53.70 | 54.37 | 55.04 |
| 52.61 | 53.29 | 53.96 | 54.64 |
| 52.32 | 52.98 | 53.64 | 54.30 |
| 52.04 | 52.68 | 53.32 | 53.96 |
| 51.75 | 52.38 | 53.00 | 53.63 |
| 51.46 | 52.07 | 52.68 | 53.29 |
| 51.18 | 51.77 | 52.36 | 52.95 |
| 50.89 | 51.46 | 52.04 | 52.61 |
| 50.61 | 51.16 | 51.71 | 52.27 |
| 50.32 | 50.86 | 51.39 | 51.93 |
| 50.61 | 51.16 | 51.71 | 52.27 |
| 50.89 | 51.46 | 52.04 | 52.61 |
| 51.18 | 51.77 | 52.36 | 52.95 |

FIG. 6(Cont.)

| | | | |
|---|---|---|---|
| 60.55 | 61.25 | 61.95 | 62.65 |
| 59.83 | 60.50 | 61.17 | 61.84 |
| 59.11 | 59.75 | 60.39 | 61.03 |
| 58.39 | 59.00 | 59.61 | 60.21 |
| 58.01 | 58.63 | 59.24 | 59.86 |
| 57.63 | 58.25 | 58.88 | 59.50 |
| 57.24 | 57.88 | 58.51 | 59.14 |
| 56.86 | 57.50 | 58.14 | 58.79 |
| 56.47 | 57.13 | 57.78 | 58.43 |
| 56.09 | 56.75 | 57.41 | 58.07 |
| 55.71 | 56.38 | 57.04 | 57.71 |
| 55.32 | 56.00 | 56.68 | 57.36 |
| 54.96 | 55.63 | 56.29 | 56.95 |
| 54.61 | 55.25 | 55.89 | 56.54 |
| 54.25 | 54.88 | 55.50 | 56.13 |
| 53.89 | 54.50 | 55.11 | 55.71 |
| 53.54 | 54.13 | 54.71 | 55.30 |
| 53.18 | 53.75 | 54.32 | 54.89 |
| 52.82 | 53.38 | 53.93 | 54.48 |
| 52.46 | 53.00 | 53.54 | 54.07 |
| 52.82 | 53.38 | 53.93 | 54.48 |
| 53.18 | 53.75 | 54.32 | 54.89 |
| 53.54 | 54.13 | 54.71 | 55.30 |

FIG. 6(Cont.)

| | | | |
|---|---|---|---|
| 63.35 | 64.05 | 64.75 | 65.46 |
| 62.51 | 63.18 | 63.85 | 64.52 |
| 61.67 | 62.30 | 62.94 | 63.58 |
| 60.82 | 61.43 | 62.04 | 62.64 |
| 60.47 | 61.09 | 61.71 | 62.32 |
| 60.13 | 60.75 | 61.38 | 62.00 |
| 59.78 | 60.41 | 61.04 | 61.68 |
| 59.43 | 60.07 | 60.71 | 61.36 |
| 59.08 | 59.73 | 60.38 | 61.04 |
| 58.73 | 59.39 | 60.05 | 60.71 |
| 58.38 | 59.05 | 59.72 | 60.39 |
| 58.04 | 58.71 | 59.39 | 60.07 |
| 57.61 | 58.27 | 58.93 | 59.59 |
| 57.18 | 57.82 | 58.46 | 59.11 |
| 56.75 | 57.38 | 58.00 | 58.63 |
| 56.32 | 56.93 | 57.54 | 58.14 |
| 55.89 | 56.48 | 57.07 | 57.66 |
| 55.46 | 56.04 | 56.61 | 57.18 |
| 55.04 | 55.59 | 56.14 | 56.70 |
| 54.61 | 55.14 | 55.68 | 56.21 |
| 55.04 | 55.59 | 56.14 | 56.70 |
| 55.46 | 56.04 | 56.61 | 57.18 |
| 55.89 | 56.48 | 57.07 | 57.66 |

FIG. 6(Cont.)

| | | | |
|---|---|---|---|
| 66.16 | 66.86 | 67.56 | 68.26 |
| 65.19 | 65.86 | 66.53 | 67.20 |
| 64.22 | 64.86 | 65.50 | 66.13 |
| 63.25 | 63.86 | 64.46 | 65.07 |
| 62.94 | 63.55 | 64.17 | 64.79 |
| 62.63 | 63.25 | 63.88 | 64.50 |
| 62.31 | 62.95 | 63.58 | 64.21 |
| 62.00 | 62.64 | 63.29 | 63.93 |
| 61.69 | 62.34 | 62.99 | 63.64 |
| 61.38 | 62.04 | 62.70 | 63.36 |
| 61.06 | 61.73 | 62.40 | 63.07 |
| 60.75 | 61.43 | 62.1 | 62.79 |
| 60.25 | 60.91 | 61.57 | 62.23 |
| 59.75 | 60.39 | 61.04 | 61.68 |
| 59.25 | 59.88 | 60.50 | 61.13 |
| 58.75 | 59.36 | 59.96 | 60.57 |
| 58.25 | 58.84 | 59.43 | 60.02 |
| 57.75 | 58.32 | 58.89 | 59.46 |
| 57.25 | 57.80 | 58.36 | 58.91 |
| 56.75 | 57.29 | 57.82 | 58.36 |
| 57.25 | 57.80 | 58.36 | 58.91 |
| 57.75 | 58.32 | 58.89 | 59.46 |
| 58.25 | 58.84 | 59.43 | 60.02 |

FIG. 6(Cont.)

| | | | |
|---|---|---|---|
| 68.96 | 69.66 | 70.36 | 71.06 |
| 67.87 | 68.54 | 69.21 | 69.88 |
| 66.77 | 67.41 | 68.05 | 68.69 |
| 65.68 | 66.29 | 66.89 | 67.50 |
| 65.40 | 66.02 | 66.63 | 67.25 |
| 65.13 | 65.75 | 66.38 | 67.00 |
| 64.85 | 65.48 | 66.12 | 66.75 |
| 64.57 | 65.21 | 65.86 | 66.50 |
| 64.29 | 64.95 | 65.60 | 66.25 |
| 64.02 | 64.68 | 65.34 | 66.00 |
| 63.74 | 64.41 | 65.08 | 65.75 |
| 63.46 | 64.14 | 64.82 | 65.50 |
| 62.89 | 63.55 | 64.21 | 64.88 |
| 62.32 | 62.96 | 63.61 | 64.25 |
| 61.75 | 62.38 | 63.00 | 63.63 |
| 61.18 | 61.79 | 62.39 | 63.00 |
| 60.61 | 61.20 | 61.79 | 62.38 |
| 60.04 | 60.61 | 61.18 | 61.75 |
| 59.46 | 60.02 | 60.57 | 61.13 |
| 58.89 | 59.43 | 59.96 | 60.50 |
| 59.46 | 60.02 | 60.57 | 61.13 |
| 60.04 | 60.61 | 61.18 | 61.75 |
| 60.61 | 61.20 | 61.79 | 62.38 |

FIG. 6(Cont.)

| | | | | |
|---|---|---|---|---|
| 71.76 | 72.46 | 74.45 | 73.87 | 74.57 |
| 70.54 | 71.21 | 73.17 | 72.55 | 73.22 |
| 69.33 | 69.96 | 71.88 | 71.24 | 71.88 |
| 68.11 | 68.71 | 70.60 | 69.98 | 70.54 |
| 67.87 | 68.48 | 69.32 | 69.71 | 70.33 |
| 67.63 | 68.25 | 69.10 | 69.50 | 70.13 |
| 67.38 | 68.02 | 68.88 | 69.29 | 69.92 |
| 67.14 | 67.79 | 68.65 | 69.07 | 69.71 |
| 66.90 | 67.55 | 68.43 | 68.86 | 69.51 |
| 66.66 | 67.32 | 68.21 | 68.64 | 69.30 |
| 66.42 | 67.09 | 67.98 | 68.43 | 69.10 |
| 66.18 | 66.86 | 67.76 | 68.21 | 68.89 |
| 65.54 | 66.20 | 67.54 | 67.52 | 68.18 |
| 64.89 | 65.54 | 66.86 | 66.82 | 67.46 |
| 64.25 | 64.88 | 66.18 | 66.13 | 66.75 |
| 63.61 | 64.21 | 65.82 | 65.43 | 66.04 |
| 62.96 | 63.55 | 64.14 | 64.73 | 65.32 |
| 62.32 | 62.89 | 63.46 | 64.04 | 64.61 |
| 61.68 | 62.23 | 62.79 | 63.34 | 63.89 |
| 61.04 | 61.57 | 62.11 | 62.64 | 63.18 |
| 61.68 | 62.23 | 62.79 | 63.34 | 63.89 |
| 62.32 | 62.89 | 63.46 | 64.04 | 64.61 |
| 62.96 | 63.55 | 64.14 | 64.73 | 65.32 |

FIG. 6(Cont.)

| | | | | |
|---|---|---|---|---|
| 75.27 | 75.97 | 76.67 | 77.37 | 78.07 |
| 73.89 | 74.56 | 75.23 | 75.90 | 76.57 |
| 72.52 | 73.16 | 73.79 | 74.43 | 75.07 |
| 71.14 | 71.75 | 72.36 | 72.96 | 73.57 |
| 70.95 | 71.56 | 72.18 | 72.79 | 73.41 |
| 70.75 | 71.38 | 72.00 | 72.63 | 73.25 |
| 70.55 | 71.19 | 71.82 | 72.46 | 73.09 |
| 70.36 | 71.00 | 71.64 | 72.29 | 72.93 |
| 70.16 | 70.81 | 71.46 | 72.12 | 72.77 |
| 69.96 | 70.63 | 71.29 | 71.95 | 72.61 |
| 69.77 | 70.44 | 71.11 | 71.78 | 72.45 |
| 69.57 | 70.25 | 70.93 | 71.61 | 72.29 |
| 68.84 | 69.50 | 70.16 | 70.82 | 71.48 |
| 68.11 | 68.75 | 69.39 | 70.04 | 70.68 |
| 67.38 | 68.00 | 68.63 | 69.25 | 69.88 |
| 66.64 | 67.25 | 67.86 | 68.46 | 69.07 |
| 65.91 | 66.50 | 67.09 | 67.68 | 68.27 |
| 65.18 | 65.75 | 66.32 | 66.89 | 67.46 |
| 64.45 | 65.00 | 65.55 | 66.11 | 66.66 |
| 63.71 | 64.25 | 64.79 | 65.32 | 65.86 |
| 64.45 | 65.00 | 65.55 | 66.11 | 66.66 |
| 65.18 | 65.75 | 66.32 | 66.89 | 67.46 |
| 65.91 | 66.50 | 67.09 | 67.68 | 68.27 |

FIG. 6(Cont.)

| | | | |
|---|---|---|---|
| 78.77 | 79.47 | 80.17 | 80.88 |
| 77.24 | 77.91 | 78.58 | 79.25 |
| 75.71 | 76.35 | 76.99 | 77.63 |
| 74.18 | 74.79 | 75.39 | 76.00 |
| 74.03 | 74.64 | 75.26 | 75.88 |
| 73.88 | 74.50 | 75.13 | 75.75 |
| 73.72 | 74.36 | 74.99 | 75.63 |
| 73.57 | 74.21 | 74.86 | 75.50 |
| 73.42 | 74.07 | 74.72 | 75.38 |
| 73.27 | 73.93 | 74.59 | 75.25 |
| 73.12 | 73.79 | 74.46 | 75.13 |
| 72.96 | 73.64 | 74.32 | 75.00 |
| 72.14 | 72.80 | 73.46 | 74.13 |
| 71.32 | 71.96 | 72.61 | 73.25 |
| 70.50 | 71.13 | 71.75 | 72.38 |
| 69.68 | 70.29 | 70.89 | 71.50 |
| 68.86 | 69.45 | 70.04 | 70.63 |
| 68.04 | 68.61 | 69.18 | 69.75 |
| 67.21 | 67.77 | 68.32 | 68.88 |
| 66.39 | 66.93 | 67.46 | 68.00 |
| 67.21 | 67.77 | 68.32 | 68.88 |
| 68.04 | 68.61 | 69.18 | 69.75 |
| 68.86 | 69.45 | 70.04 | 70.63 |

FIG. 6

| Position Number (in.) | Outer Longitudinal Cubic-Ref Number | Inner Logitudinal Cubic-Ref Number | Outer Latitudinal Cubic-Ref Number |
|---|---|---|---|
| 1 | | | |
| 2 | | | |
| 3 | | | 6.15 |
| 4 | | | 6.04 |
| 5 | | | 5.94 |
| 6 | | | 5.83 |
| 7 | | | 5.73 |
| 8 | | | 5.63 |
| 9 | | | 5.52 |
| 10 | | | 5.42 |
| 11 | | | 5.31 |
| 12 | | | 5.21 |
| 13 | | | 5.10 |
| 14 | -0.63 | -0.63 | 5.00 |
| 15 | | | 4.90 |
| 16 | | | 4.79 |
| 17 | | | 4.69 |
| 18 | | | 4.58 |
| 19 | | | 4.48 |
| 20 | | | 4.38 |
| 21 | | | 4.27 |
| 22 | -1.25 | -1.25 | 4.17 |
| 23 | | | 3.96 |

FIG. 7(Cont.)

| Inner Latitudinal Cubic-Ref Number | | Outer Edge | 1 | 2 | 3 | 4 |
|---|---|---|---|---|---|---|
| | | -1.43 | 98.75 | 92.60 | 86.46 | 80.31 | 74.17 |
| | | -1.43 | 99.38 | 93.23 | 87.08 | 80.94 | 74.79 |
| | | -1.43 | 100.00 | 93.85 | 87.71 | 81.56 | 75.42 |
| | | -1.43 | 100.00 | 93.96 | 87.92 | 81.88 | 75.83 |
| | | -1.43 | 100.00 | 94.06 | 88.13 | 82.19 | 76.25 |
| | | -1.43 | 100.00 | 94.17 | 88.33 | 82.50 | 76.67 |
| | | -1.43 | 100.00 | 94.27 | 88.54 | 82.81 | 77.08 |
| | | -1.43 | 100.00 | 94.38 | 88.75 | 83.13 | 77.50 |
| | | -1.43 | 100.00 | 94.48 | 88.96 | 83.44 | 77.92 |
| | | -1.43 | 100.00 | 94.58 | 89.17 | 83.75 | 78.33 |
| | | -1.43 | 100.00 | 94.69 | 89.38 | 84.06 | 78.75 |
| | | -1.43 | 100.00 | 94.79 | 89.58 | 84.38 | 79.17 |
| | | -1.43 | 100.00 | 94.90 | 89.79 | 84.69 | 79.58 |
| | | -1.43 | 100.00 | 95.00 | 90.00 | 85.00 | 80.00 |
| | | -1.43 | 100.00 | 95.10 | 90.21 | 85.31 | 80.42 |
| | | -1.43 | 100.00 | 95.21 | 90.42 | 85.63 | 80.83 |
| | | -1.43 | 100.00 | 95.31 | 90.63 | 85.94 | 81.25 |
| | | -1.43 | 100.00 | 95.42 | 90.83 | 86.25 | 81.67 |
| | | -1.43 | 100.00 | 95.52 | 91.04 | 86.56 | 82.08 |
| | | -1.43 | 100.00 | 95.63 | 91.25 | 86.88 | 82.50 |
| | | -1.43 | 100.00 | 95.73 | 91.46 | 87.19 | 82.92 |
| | | -1.43 | 100.00 | 95.83 | 91.67 | 87.50 | 83.33 |
| | | -1.43 | 100.00 | 96.04 | 92.08 | 88.13 | 84.17 |

FIG. 7(Cont.)

| 5 | 6 - Outer Value | 7 | 8 | 9 | 10 | 11 | 12 | 13 |
|---|---|---|---|---|---|---|---|---|
| 68.02 | 61.88 | 63.30 | 64.73 | 66.16 | 67.59 | 69.02 | 70.45 | 71.88 |
| 68.65 | 62.50 | 63.93 | 65.36 | 66.79 | 68.21 | 69.64 | 71.07 | 72.50 |
| 69.27 | 63.13 | 64.55 | 65.98 | 67.41 | 68.84 | 70.27 | 71.70 | 73.13 |
| 69.79 | 63.75 | 65.18 | 66.61 | 68.04 | 69.46 | 70.89 | 72.32 | 73.75 |
| 70.31 | 64.38 | 65.80 | 67.23 | 68.66 | 70.09 | 71.52 | 72.95 | 74.38 |
| 70.83 | 65.00 | 66.43 | 67.86 | 69.29 | 70.71 | 72.14 | 73.57 | 75.00 |
| 71.35 | 65.63 | 67.05 | 68.48 | 69.91 | 71.34 | 72.77 | 74.20 | 75.63 |
| 71.88 | 66.25 | 67.68 | 69.11 | 70.54 | 71.96 | 73.39 | 74.82 | 76.25 |
| 72.40 | 66.88 | 68.30 | 69.73 | 71.16 | 72.59 | 74.02 | 75.45 | 76.88 |
| 72.92 | 67.50 | 68.93 | 70.36 | 71.79 | 73.21 | 74.64 | 76.07 | 77.50 |
| 73.44 | 68.13 | 69.55 | 70.98 | 72.41 | 73.84 | 75.27 | 76.70 | 78.13 |
| 73.96 | 68.75 | 70.18 | 71.61 | 73.04 | 74.46 | 75.89 | 77.32 | 78.75 |
| 74.48 | 69.38 | 70.80 | 72.23 | 73.66 | 75.09 | 76.52 | 77.95 | 79.38 |
| 75.00 | 70.00 | 71.43 | 72.86 | 74.29 | 75.71 | 77.14 | 78.57 | 80.00 |
| 75.52 | 70.63 | 72.05 | 73.48 | 74.91 | 76.34 | 77.77 | 79.20 | 80.63 |
| 76.04 | 71.25 | 72.68 | 74.11 | 75.54 | 76.96 | 78.39 | 79.82 | 81.25 |
| 76.56 | 71.88 | 73.30 | 74.73 | 76.16 | 77.59 | 79.02 | 80.45 | 81.88 |
| 77.08 | 72.50 | 73.93 | 75.36 | 76.79 | 78.21 | 79.64 | 81.07 | 82.50 |
| 77.60 | 73.13 | 74.55 | 75.98 | 77.41 | 78.84 | 80.27 | 81.70 | 83.13 |
| 78.13 | 73.75 | 75.18 | 76.61 | 78.04 | 79.46 | 80.89 | 82.32 | 83.75 |
| 78.65 | 74.38 | 75.80 | 77.23 | 78.66 | 80.09 | 81.52 | 82.95 | 84.38 |
| 79.17 | 75.00 | 76.43 | 77.86 | 79.29 | 80.71 | 82.14 | 83.57 | 85.00 |
| 80.21 | 76.25 | 77.68 | 79.11 | 80.54 | 81.96 | 83.39 | 84.82 | 86.25 |

FIG. 7(Cont.)

| 14 | 15 | 16 | 17 | 18 | 19 | 20 | 21 | 22 |
|---|---|---|---|---|---|---|---|---|
| 73.30 | 74.73 | 76.16 | 77.59 | 79.02 | 80.45 | 81.88 | 83.30 | 84.73 |
| 73.93 | 75.36 | 76.79 | 78.21 | 79.64 | 81.07 | 82.50 | 83.93 | 85.36 |
| 74.55 | 75.98 | 77.41 | 78.84 | 80.27 | 81.70 | 83.13 | 84.55 | 85.98 |
| 75.18 | 76.61 | 78.04 | 79.46 | 80.89 | 82.32 | 83.75 | 85.18 | 86.61 |
| 75.80 | 77.23 | 78.66 | 80.09 | 81.52 | 82.95 | 84.38 | 85.80 | 87.23 |
| 76.43 | 77.86 | 79.29 | 80.71 | 82.14 | 83.57 | 85.00 | 86.43 | 87.86 |
| 77.05 | 78.48 | 79.91 | 81.34 | 82.77 | 84.20 | 85.63 | 87.05 | 88.48 |
| 77.68 | 79.11 | 80.54 | 81.96 | 83.39 | 84.82 | 86.25 | 87.68 | 89.11 |
| 78.30 | 79.73 | 81.16 | 82.59 | 84.02 | 85.45 | 86.88 | 88.30 | 89.73 |
| 78.93 | 80.36 | 81.79 | 83.21 | 84.64 | 86.07 | 87.50 | 88.93 | 90.36 |
| 79.55 | 80.98 | 82.41 | 83.84 | 85.27 | 86.70 | 88.13 | 89.55 | 90.98 |
| 80.18 | 81.61 | 83.04 | 84.46 | 85.89 | 87.32 | 88.75 | 90.18 | 91.61 |
| 80.80 | 82.23 | 83.66 | 85.09 | 86.52 | 87.95 | 89.38 | 90.80 | 92.23 |
| 81.43 | 82.86 | 84.29 | 85.71 | 87.14 | 88.57 | 90.00 | 91.43 | 92.86 |
| 82.05 | 83.48 | 84.91 | 86.34 | 87.77 | 89.20 | 90.63 | 92.05 | 93.48 |
| 82.68 | 84.11 | 85.54 | 86.96 | 88.39 | 89.82 | 91.25 | 92.68 | 94.11 |
| 83.30 | 84.73 | 86.16 | 87.59 | 89.02 | 90.45 | 91.88 | 93.30 | 94.73 |
| 83.93 | 85.36 | 86.79 | 88.21 | 89.64 | 91.07 | 92.50 | 93.93 | 95.36 |
| 84.55 | 85.98 | 87.41 | 88.84 | 90.27 | 91.70 | 93.13 | 94.55 | 95.98 |
| 85.18 | 86.61 | 88.04 | 89.46 | 90.89 | 92.32 | 93.75 | 95.18 | 96.61 |
| 85.80 | 87.23 | 88.66 | 90.09 | 91.52 | 92.95 | 94.38 | 95.80 | 97.23 |
| 86.43 | 87.86 | 89.29 | 90.71 | 92.14 | 93.57 | 95.00 | 96.43 | 97.86 |
| 87.68 | 89.11 | 90.54 | 91.96 | 93.39 | 94.82 | 96.25 | 97.68 | 99.11 |

FIG. 7(Cont.)

| 23 | 24 | 25 | 26 | 27 | 28 | 29 | 30 | 31 |
|---|---|---|---|---|---|---|---|---|
| 86.16 | 87.59 | 89.02 | 90.45 | 91.88 | 93.30 | 94.73 | 96.16 | 97.59 |
| 86.79 | 88.21 | 89.64 | 91.07 | 92.50 | 93.93 | 95.36 | 96.79 | 98.21 |
| 87.41 | 88.84 | 90.27 | 91.70 | 93.13 | 94.55 | 95.98 | 97.41 | 98.84 |
| 88.04 | 89.46 | 90.89 | 92.32 | 93.75 | 95.18 | 96.61 | 98.04 | 99.46 |
| 88.66 | 90.09 | 91.52 | 92.95 | 94.38 | 95.80 | 97.23 | 98.66 | 100.09 |
| 89.29 | 90.71 | 92.14 | 93.57 | 95.00 | 96.43 | 97.86 | 99.29 | 100.71 |
| 89.91 | 91.34 | 92.77 | 94.20 | 95.63 | 97.05 | 98.48 | 99.91 | 101.34 |
| 90.54 | 91.96 | 93.39 | 94.82 | 96.25 | 97.68 | 99.11 | 100.54 | 101.96 |
| 91.16 | 92.59 | 94.02 | 95.45 | 96.88 | 98.30 | 99.73 | 101.16 | 102.59 |
| 91.79 | 93.21 | 94.64 | 96.07 | 97.50 | 98.93 | 100.36 | 101.79 | 103.21 |
| 92.41 | 93.84 | 95.27 | 96.70 | 98.13 | 99.55 | 100.98 | 102.41 | 103.84 |
| 93.04 | 94.46 | 95.89 | 97.32 | 98.75 | 100.18 | 101.61 | 103.04 | 104.46 |
| 93.66 | 95.09 | 96.52 | 97.95 | 99.38 | 100.80 | 102.23 | 103.66 | 105.09 |
| 94.29 | 95.71 | 97.14 | 98.57 | 100.00 | 101.43 | 102.86 | 104.29 | 105.71 |
| 94.91 | 96.34 | 97.77 | 99.20 | 100.63 | 102.05 | 103.48 | 104.91 | 106.34 |
| 95.54 | 96.96 | 98.39 | 99.82 | 101.25 | 102.68 | 104.11 | 105.54 | 106.96 |
| 96.16 | 97.59 | 99.02 | 100.45 | 101.88 | 103.30 | 104.73 | 106.16 | 107.59 |
| 96.79 | 98.21 | 99.64 | 101.07 | 102.50 | 103.93 | 105.36 | 106.79 | 108.21 |
| 97.41 | 98.84 | 100.27 | 101.70 | 103.13 | 104.55 | 105.98 | 107.41 | 108.84 |
| 98.04 | 99.46 | 100.89 | 102.32 | 103.75 | 105.18 | 106.61 | 108.04 | 109.46 |
| 98.66 | 100.09 | 101.52 | 102.95 | 104.38 | 105.80 | 107.23 | 108.66 | 110.09 |
| 99.29 | 100.71 | 102.14 | 103.57 | 105.00 | 106.43 | 107.86 | 109.29 | 110.71 |
| 100.54 | 101.96 | 103.39 | 104.82 | 106.25 | 107.68 | 109.11 | 110.54 | 111.96 |

FIG. 7(Cont.)

| 32 | 33 | 34 - Center Value | 33 | 32 | 31 | 30 | 29 | 28 |
|---|---|---|---|---|---|---|---|---|
| 99.02 | 100.45 | 101.88 | 100.45 | 99.02 | 97.59 | 96.16 | 94.73 | 93.30 |
| 99.64 | 101.07 | 102.50 | 101.07 | 99.64 | 98.21 | 96.79 | 95.36 | 93.93 |
| 100.27 | 101.70 | 103.13 | 101.70 | 100.27 | 98.84 | 97.41 | 95.98 | 94.55 |
| 100.89 | 102.32 | 103.75 | 102.32 | 100.89 | 99.46 | 98.04 | 96.61 | 95.18 |
| 101.52 | 102.95 | 104.38 | 102.95 | 101.52 | 100.09 | 98.66 | 97.23 | 95.80 |
| 102.14 | 103.57 | 105.00 | 103.57 | 102.14 | 100.71 | 99.29 | 97.86 | 96.43 |
| 102.77 | 104.20 | 105.63 | 104.20 | 102.77 | 101.34 | 99.91 | 98.48 | 97.05 |
| 103.39 | 104.82 | 106.25 | 104.82 | 103.39 | 101.96 | 100.54 | 99.11 | 97.68 |
| 104.02 | 105.45 | 106.88 | 105.45 | 104.02 | 102.59 | 101.16 | 99.73 | 98.30 |
| 104.64 | 106.07 | 107.50 | 106.07 | 104.64 | 103.21 | 101.79 | 100.36 | 98.93 |
| 105.27 | 106.70 | 108.13 | 106.70 | 105.27 | 103.84 | 102.41 | 100.98 | 99.55 |
| 105.89 | 107.32 | 108.75 | 107.32 | 105.89 | 104.46 | 103.04 | 101.61 | 100.18 |
| 106.52 | 107.95 | 109.38 | 107.95 | 106.52 | 105.09 | 103.66 | 102.23 | 100.80 |
| 107.14 | 108.57 | 110.00 | 108.57 | 107.14 | 105.71 | 104.29 | 102.86 | 101.43 |
| 107.77 | 109.20 | 110.63 | 109.20 | 107.77 | 106.34 | 104.91 | 103.48 | 102.05 |
| 108.39 | 109.82 | 111.25 | 109.82 | 108.39 | 106.96 | 105.54 | 104.11 | 102.68 |
| 109.02 | 110.45 | 111.88 | 110.45 | 109.02 | 107.59 | 106.16 | 104.73 | 103.30 |
| 109.64 | 111.07 | 112.50 | 111.07 | 109.64 | 108.21 | 106.79 | 105.36 | 103.93 |
| 110.27 | 111.70 | 113.13 | 111.70 | 110.27 | 108.84 | 107.41 | 105.98 | 104.55 |
| 110.89 | 112.32 | 113.75 | 112.32 | 110.89 | 109.46 | 108.04 | 106.61 | 105.18 |
| 111.52 | 112.95 | 114.38 | 112.95 | 111.52 | 110.09 | 108.66 | 107.23 | 105.80 |
| 112.14 | 113.57 | 115.00 | 113.57 | 112.14 | 110.71 | 109.29 | 107.86 | 106.43 |
| 113.39 | 114.82 | 116.25 | 114.82 | 113.39 | 111.96 | 110.54 | 109.11 | 107.68 |

FIG. 7(Cont.)

| 27 | 26 | 25 | 24 | 23 | 22 | 21 | 20 | 19 |
|---|---|---|---|---|---|---|---|---|
| 91.88 | 90.45 | 89.02 | 87.59 | 86.16 | 84.73 | 83.30 | 81.88 | 80.45 |
| 92.50 | 91.07 | 89.64 | 88.21 | 86.79 | 85.36 | 83.93 | 82.50 | 81.07 |
| 93.13 | 91.70 | 90.27 | 88.84 | 87.41 | 85.98 | 84.55 | 83.13 | 81.70 |
| 93.75 | 92.32 | 90.89 | 89.46 | 88.04 | 86.61 | 85.18 | 83.75 | 82.32 |
| 94.38 | 92.95 | 91.52 | 90.09 | 88.66 | 87.23 | 85.80 | 84.38 | 82.95 |
| 95.00 | 93.57 | 92.14 | 90.71 | 89.29 | 87.86 | 86.43 | 85.00 | 83.57 |
| 95.63 | 94.20 | 92.77 | 91.34 | 89.91 | 88.48 | 87.05 | 85.63 | 84.20 |
| 96.25 | 94.82 | 93.39 | 91.96 | 90.54 | 89.11 | 87.68 | 86.25 | 84.82 |
| 96.88 | 95.45 | 94.02 | 92.59 | 91.16 | 89.73 | 88.30 | 86.88 | 85.45 |
| 97.50 | 96.07 | 94.64 | 93.21 | 91.79 | 90.36 | 88.93 | 87.50 | 86.07 |
| 98.13 | 96.70 | 95.27 | 93.84 | 92.41 | 90.98 | 89.55 | 88.13 | 86.70 |
| 98.75 | 97.32 | 95.89 | 94.46 | 93.04 | 91.61 | 90.18 | 88.75 | 87.32 |
| 99.38 | 97.95 | 96.52 | 95.09 | 93.66 | 92.23 | 90.80 | 89.38 | 87.95 |
| 100.00 | 98.57 | 97.14 | 95.71 | 94.29 | 92.86 | 91.43 | 90.00 | 88.57 |
| 100.63 | 99.20 | 97.77 | 96.34 | 94.91 | 93.48 | 92.05 | 90.63 | 89.20 |
| 101.25 | 99.82 | 98.39 | 96.96 | 95.54 | 94.11 | 92.68 | 91.25 | 89.82 |
| 101.88 | 100.45 | 99.02 | 97.59 | 96.16 | 94.73 | 93.30 | 91.88 | 90.45 |
| 102.50 | 101.07 | 99.64 | 98.21 | 96.79 | 95.36 | 93.93 | 92.50 | 91.07 |
| 103.13 | 101.70 | 100.27 | 98.84 | 97.41 | 95.98 | 94.55 | 93.13 | 91.70 |
| 103.75 | 102.32 | 100.89 | 99.46 | 98.04 | 96.61 | 95.18 | 93.75 | 92.32 |
| 104.38 | 102.95 | 101.52 | 100.09 | 98.66 | 97.23 | 95.80 | 94.38 | 92.95 |
| 105.00 | 103.57 | 102.14 | 100.71 | 99.29 | 97.86 | 96.43 | 95.00 | 93.57 |
| 106.25 | 104.82 | 103.39 | 101.96 | 100.54 | 99.11 | 97.68 | 96.25 | 94.82 |

FIG. 7(Cont.)

| 18 | 17 | 16 | 15 | 14 | 13 | 12 | 11 | 10 |
|---|---|---|---|---|---|---|---|---|
| 79.02 | 77.59 | 76.16 | 74.73 | 73.30 | 71.88 | 70.45 | 69.02 | 67.59 |
| 79.64 | 78.21 | 76.79 | 75.36 | 73.93 | 72.50 | 71.07 | 69.64 | 68.21 |
| 80.27 | 78.84 | 77.41 | 75.98 | 74.55 | 73.13 | 71.70 | 70.27 | 68.84 |
| 80.89 | 79.46 | 78.04 | 76.61 | 75.18 | 73.75 | 72.32 | 70.89 | 69.46 |
| 81.52 | 80.09 | 78.66 | 77.23 | 75.80 | 74.38 | 72.95 | 71.52 | 70.09 |
| 82.14 | 80.71 | 79.29 | 77.86 | 76.43 | 75.00 | 73.57 | 72.14 | 70.71 |
| 82.77 | 81.34 | 79.91 | 78.48 | 77.05 | 75.63 | 74.20 | 72.77 | 71.34 |
| 83.39 | 81.96 | 80.54 | 79.11 | 77.68 | 76.25 | 74.82 | 73.39 | 71.96 |
| 84.02 | 82.59 | 81.16 | 79.73 | 78.30 | 76.88 | 75.45 | 74.02 | 72.59 |
| 84.64 | 83.21 | 81.79 | 80.36 | 78.93 | 77.50 | 76.07 | 74.64 | 73.21 |
| 85.27 | 83.84 | 82.41 | 80.98 | 79.55 | 78.13 | 76.70 | 75.27 | 73.84 |
| 85.89 | 84.46 | 83.04 | 81.61 | 80.18 | 78.75 | 77.32 | 75.89 | 74.46 |
| 86.52 | 85.09 | 83.66 | 82.23 | 80.80 | 79.38 | 77.95 | 76.52 | 75.09 |
| 87.14 | 85.71 | 84.29 | 82.86 | 81.43 | 80.00 | 78.57 | 77.14 | 75.71 |
| 87.77 | 86.34 | 84.91 | 83.48 | 82.05 | 80.63 | 79.20 | 77.77 | 76.34 |
| 88.39 | 86.96 | 85.54 | 84.11 | 82.68 | 81.25 | 79.82 | 78.39 | 76.96 |
| 89.02 | 87.59 | 86.16 | 84.73 | 83.30 | 81.88 | 80.45 | 79.02 | 77.59 |
| 89.64 | 88.21 | 86.79 | 85.36 | 83.93 | 82.50 | 81.07 | 79.64 | 78.21 |
| 90.27 | 88.84 | 87.41 | 85.98 | 84.55 | 83.13 | 81.70 | 80.27 | 78.84 |
| 90.89 | 89.46 | 88.04 | 86.61 | 85.18 | 83.75 | 82.32 | 80.89 | 79.46 |
| 91.52 | 90.09 | 88.66 | 87.23 | 85.80 | 84.38 | 82.95 | 81.52 | 80.09 |
| 92.14 | 90.71 | 89.29 | 87.86 | 86.43 | 85.00 | 83.57 | 82.14 | 80.71 |
| 93.39 | 91.96 | 90.54 | 89.11 | 87.68 | 86.25 | 84.82 | 83.39 | 81.96 |

FIG. 7(Cont.)

| 9 | 8 | 7 | 6 | 5 | 4 | 3 | 2 | 1 | Outer Edge |
|---|---|---|---|---|---|---|---|---|---|
| 66.16 | 64.73 | 63.30 | 61.88 | 68.02 | 74.17 | 80.31 | 86.46 | 92.60 | 98.75 |
| 66.79 | 65.36 | 63.93 | 62.50 | 68.65 | 74.79 | 80.94 | 87.08 | 93.23 | 99.38 |
| 67.41 | 65.98 | 64.55 | 63.13 | 69.27 | 75.42 | 81.56 | 87.71 | 93.85 | 100.00 |
| 68.04 | 66.61 | 65.18 | 63.75 | 69.79 | 75.83 | 81.88 | 87.92 | 93.96 | 100.00 |
| 68.66 | 67.23 | 65.80 | 64.38 | 70.31 | 76.25 | 82.19 | 88.13 | 94.06 | 100.00 |
| 69.29 | 67.86 | 66.43 | 65.00 | 70.83 | 76.67 | 82.50 | 88.33 | 94.17 | 100.00 |
| 69.91 | 68.48 | 67.05 | 65.63 | 71.35 | 77.08 | 82.81 | 88.54 | 94.27 | 100.00 |
| 70.54 | 69.11 | 67.68 | 66.25 | 71.88 | 77.50 | 83.13 | 88.75 | 94.38 | 100.00 |
| 71.16 | 69.73 | 68.30 | 66.88 | 72.40 | 77.92 | 83.44 | 88.96 | 94.48 | 100.00 |
| 71.79 | 70.36 | 68.93 | 67.50 | 72.92 | 78.33 | 83.75 | 89.17 | 94.58 | 100.00 |
| 72.41 | 70.98 | 69.55 | 68.13 | 73.44 | 78.75 | 84.06 | 89.38 | 94.69 | 100.00 |
| 73.04 | 71.61 | 70.18 | 68.75 | 73.96 | 79.17 | 84.38 | 89.58 | 94.79 | 100.00 |
| 73.66 | 72.23 | 70.80 | 69.38 | 74.48 | 79.58 | 84.69 | 89.79 | 94.90 | 100.00 |
| 74.29 | 72.86 | 71.43 | 70.00 | 75.00 | 80.00 | 85.00 | 90.00 | 95.00 | 100.00 |
| 74.91 | 73.48 | 72.05 | 70.63 | 75.52 | 80.42 | 85.31 | 90.21 | 95.10 | 100.00 |
| 75.54 | 74.11 | 72.68 | 71.25 | 76.04 | 80.83 | 85.63 | 90.42 | 95.21 | 100.00 |
| 76.16 | 74.73 | 73.30 | 71.88 | 76.56 | 81.25 | 85.94 | 90.63 | 95.31 | 100.00 |
| 76.79 | 75.36 | 73.93 | 72.50 | 77.08 | 81.67 | 86.25 | 90.83 | 95.42 | 100.00 |
| 77.41 | 75.98 | 74.55 | 73.13 | 77.60 | 82.08 | 86.56 | 91.04 | 95.52 | 100.00 |
| 78.04 | 76.61 | 75.18 | 73.75 | 78.13 | 82.50 | 86.88 | 91.25 | 95.63 | 100.00 |
| 78.66 | 77.23 | 75.80 | 74.38 | 78.65 | 82.92 | 87.19 | 91.46 | 95.73 | 100.00 |
| 79.29 | 77.86 | 76.43 | 75.00 | 79.17 | 83.33 | 87.50 | 91.67 | 95.83 | 100.00 |
| 80.54 | 79.11 | 77.68 | 76.25 | 80.21 | 84.17 | 88.13 | 92.08 | 96.04 | 100.00 |

FIG. 7(Cont.)

| | | | |
|---|---|---|---|
| 24 | | | 3.75 |
| 25 | | | 3.54 |
| 26 | | | 3.33 |
| 27 | | | 3.13 |
| 28 | | | 2.92 |
| 29 | | | 2.71 |
| 30 | 1.88 | 0.63 | 2.50 |
| 31 | | | 2.81 |
| 32 | | | 1.99 |
| 33 | | | 1.17 |
| 34 | | | 0.35 |
| 35 | | | -0.47 |
| 36 | | | -1.29 |
| 37 | | | -2.11 |
| 38 | -1.00 | 0.63 | -2.93 |
| 39 | | | -4.23 |
| 40 | | | -5.53 |
| 41 | | | -6.83 |
| 42 | | | -7.00 |
| 43 | | | -7.17 |
| 44 | | | -7.33 |
| 45 | | | -7.50 |
| 46 | 1.63 | 3.13 | -7.67 |
| 47 | | | -7.40 |

FIG. 7(Cont.)

| | | | | | | |
|---|---|---|---|---|---|---|
| | -1.43 | 100.00 | 96.25 | 92.50 | 88.75 | 85.00 |
| | -1.43 | 100.00 | 96.46 | 92.92 | 89.38 | 85.83 |
| | -1.43 | 100.00 | 96.67 | 93.33 | 90.00 | 86.67 |
| | -1.43 | 100.00 | 96.88 | 93.75 | 90.63 | 87.50 |
| | -1.43 | 100.00 | 97.08 | 94.17 | 91.25 | 88.33 |
| | -1.43 | 100.00 | 97.29 | 94.58 | 91.88 | 89.17 |
| | -1.43 | 100.00 | 97.50 | 95.00 | 92.50 | 90.00 |
| | -1.47 | 100.00 | 97.19 | 94.38 | 91.56 | 88.75 |
| | -1.52 | 93.20 | 91.21 | 89.22 | 87.23 | 85.23 |
| | -1.56 | 86.40 | 85.23 | 84.06 | 82.89 | 81.72 |
| | -1.61 | 79.60 | 79.25 | 78.90 | 78.55 | 78.20 |
| | -1.65 | 72.80 | 73.27 | 73.74 | 74.21 | 74.68 |
| | -1.70 | 66.00 | 67.29 | 68.58 | 69.88 | 71.17 |
| | -1.74 | 59.20 | 61.31 | 63.43 | 65.54 | 67.65 |
| | -1.79 | 52.40 | 55.33 | 58.27 | 61.20 | 64.13 |
| | -1.73 | 45.60 | 49.83 | 54.07 | 58.30 | 62.53 |
| | -1.67 | 38.80 | 44.33 | 49.87 | 55.40 | 60.93 |
| | -1.61 | 32.00 | 38.83 | 45.67 | 52.50 | 59.33 |
| | -1.55 | 32.00 | 39.00 | 46.00 | 53.00 | 60.00 |
| | -1.50 | 32.00 | 39.17 | 46.33 | 53.50 | 60.67 |
| | -1.44 | 32.00 | 39.33 | 46.67 | 54.00 | 61.33 |
| | -1.36 | 32.00 | 39.50 | 47.00 | 54.50 | 62.00 |
| | -1.32 | 32.00 | 39.67 | 47.33 | 55.00 | 62.67 |
| | -1.27 | 32.00 | 39.40 | 46.79 | 54.19 | 61.58 |

FIG. 7(Cont.)

| 81.25 | 77.50 | 78.93 | 80.36 | 81.79 | 83.21 | 84.64 | 86.07 | 87.50 |
|---|---|---|---|---|---|---|---|---|
| 82.29 | 78.75 | 80.18 | 81.61 | 83.04 | 84.46 | 85.89 | 87.32 | 88.75 |
| 83.33 | 80.00 | 81.43 | 82.86 | 84.29 | 85.71 | 87.14 | 88.57 | 90.00 |
| 84.38 | 81.25 | 82.68 | 84.11 | 85.54 | 86.96 | 88.39 | 89.82 | 91.25 |
| 85.42 | 82.50 | 83.93 | 85.36 | 86.79 | 88.21 | 89.64 | 91.07 | 92.50 |
| 86.46 | 83.75 | 85.18 | 86.61 | 88.04 | 89.46 | 90.89 | 92.32 | 93.75 |
| 87.50 | 85.00 | 86.43 | 87.86 | 89.29 | 90.71 | 92.14 | 93.57 | 95.00 |
| 85.94 | 83.13 | 84.60 | 86.07 | 87.54 | 89.02 | 90.49 | 91.96 | 93.44 |
| 83.24 | 81.25 | 82.77 | 84.29 | 85.80 | 87.32 | 88.84 | 90.36 | 91.88 |
| 80.55 | 79.38 | 80.94 | 82.50 | 84.06 | 85.63 | 87.19 | 88.75 | 90.31 |
| 77.85 | 77.50 | 79.11 | 80.71 | 82.32 | 83.93 | 85.54 | 87.14 | 88.75 |
| 75.15 | 75.63 | 77.28 | 78.93 | 80.58 | 82.23 | 83.88 | 85.54 | 87.19 |
| 72.46 | 73.75 | 75.45 | 77.14 | 78.84 | 80.54 | 82.23 | 83.93 | 85.63 |
| 69.76 | 71.88 | 73.62 | 75.36 | 77.10 | 78.84 | 80.58 | 82.32 | 84.06 |
| 67.07 | 70.00 | 71.79 | 73.57 | 75.36 | 77.14 | 78.93 | 80.71 | 82.50 |
| 66.77 | 71.00 | 72.73 | 74.46 | 76.18 | 77.91 | 79.64 | 81.37 | 83.09 |
| 66.47 | 72.00 | 73.67 | 75.34 | 77.01 | 78.68 | 80.35 | 82.02 | 83.69 |
| 66.17 | 73.00 | 74.61 | 76.22 | 77.83 | 79.45 | 81.06 | 82.67 | 84.28 |
| 67.00 | 74.00 | 75.55 | 77.11 | 78.66 | 80.21 | 81.77 | 83.32 | 84.88 |
| 67.83 | 75.00 | 76.50 | 77.99 | 79.49 | 80.98 | 82.48 | 83.97 | 85.47 |
| 68.67 | 76.00 | 77.44 | 78.88 | 80.31 | 81.75 | 83.19 | 84.63 | 86.06 |
| 69.50 | 77.00 | 78.36 | 79.71 | 81.07 | 82.43 | 83.79 | 85.14 | 86.50 |
| 70.33 | 78.00 | 79.32 | 80.64 | 81.96 | 83.29 | 84.61 | 85.93 | 87.25 |
| 68.98 | 76.38 | 77.64 | 78.91 | 80.18 | 81.45 | 82.71 | 83.98 | 85.25 |

FIG. 7(Cont.)

| 88.93 | 90.36 | 91.79 | 93.21 | 94.64 | 96.07 | 97.50 | 98.93 | 100.36 |
|---|---|---|---|---|---|---|---|---|
| 90.18 | 91.61 | 93.04 | 94.46 | 95.89 | 97.32 | 98.75 | 100.18 | 101.61 |
| 91.43 | 92.86 | 94.29 | 95.71 | 97.14 | 98.57 | 100.00 | 101.43 | 102.86 |
| 92.68 | 94.11 | 95.54 | 96.96 | 98.39 | 99.82 | 101.25 | 102.68 | 104.11 |
| 93.93 | 95.36 | 96.79 | 98.21 | 99.64 | 101.07 | 102.50 | 103.93 | 105.36 |
| 95.18 | 96.61 | 98.04 | 99.46 | 100.89 | 102.32 | 103.75 | 105.18 | 106.61 |
| 96.43 | 97.86 | 99.29 | 100.71 | 102.14 | 103.57 | 105.00 | 106.43 | 107.86 |
| 94.91 | 96.38 | 97.86 | 99.33 | 100.80 | 102.28 | 103.75 | 105.22 | 106.70 |
| 93.39 | 94.91 | 96.43 | 97.95 | 99.46 | 100.98 | 102.50 | 104.02 | 105.54 |
| 91.88 | 93.44 | 95.00 | 96.56 | 98.13 | 99.69 | 101.25 | 102.81 | 104.38 |
| 90.36 | 91.96 | 93.57 | 95.18 | 96.79 | 98.39 | 100.00 | 101.61 | 103.21 |
| 88.84 | 90.49 | 92.14 | 93.79 | 95.45 | 97.10 | 98.75 | 100.40 | 102.05 |
| 87.32 | 89.02 | 90.71 | 92.41 | 94.11 | 95.80 | 97.50 | 99.20 | 100.89 |
| 85.80 | 87.54 | 89.29 | 91.03 | 92.77 | 94.51 | 96.25 | 97.99 | 99.73 |
| 84.29 | 86.07 | 87.86 | 89.64 | 91.43 | 93.21 | 95.00 | 96.79 | 98.57 |
| 84.82 | 86.55 | 88.28 | 90.00 | 91.73 | 93.46 | 95.19 | 96.92 | 98.64 |
| 85.36 | 87.03 | 88.70 | 90.37 | 92.04 | 93.71 | 95.38 | 97.04 | 98.71 |
| 85.89 | 87.50 | 89.12 | 90.73 | 92.34 | 93.95 | 95.56 | 97.17 | 98.79 |
| 86.43 | 87.98 | 89.54 | 91.09 | 92.64 | 94.20 | 95.75 | 97.30 | 98.86 |
| 86.96 | 88.46 | 89.96 | 91.45 | 92.95 | 94.44 | 95.94 | 97.43 | 98.93 |
| 87.50 | 88.94 | 90.38 | 91.81 | 93.25 | 94.69 | 96.13 | 97.56 | 99.00 |
| 87.86 | 89.21 | 90.57 | 91.93 | 93.29 | 94.64 | 96.00 | 97.36 | 98.71 |
| 88.57 | 89.89 | 91.21 | 92.54 | 93.86 | 95.18 | 96.50 | 97.82 | 99.14 |
| 86.52 | 87.79 | 89.05 | 90.32 | 91.59 | 92.86 | 94.12 | 95.39 | 96.66 |

FIG. 7(Cont.)

| | | | | | | | |
|---|---|---|---|---|---|---|---|
| 101.79 | 103.21 | 104.64 | 106.07 | 107.50 | 108.93 | 110.36 | 111.79 | 113.21 |
| 103.04 | 104.46 | 105.89 | 107.32 | 108.75 | 110.18 | 111.61 | 113.04 | 114.46 |
| 104.29 | 105.71 | 107.14 | 108.57 | 110.00 | 111.43 | 112.86 | 114.29 | 115.71 |
| 105.54 | 106.96 | 108.39 | 109.82 | 111.25 | 112.68 | 114.11 | 115.54 | 116.96 |
| 106.79 | 108.21 | 109.64 | 111.07 | 112.50 | 113.93 | 115.36 | 116.79 | 118.21 |
| 108.04 | 109.46 | 110.89 | 112.32 | 113.75 | 115.18 | 116.61 | 118.04 | 119.46 |
| 109.29 | 110.71 | 112.14 | 113.57 | 115.00 | 116.43 | 117.86 | 119.29 | 120.71 |
| 108.17 | 109.64 | 111.12 | 112.59 | 114.06 | 115.54 | 117.01 | 118.48 | 119.96 |
| 107.05 | 108.57 | 110.09 | 111.61 | 113.13 | 114.64 | 116.16 | 117.68 | 119.20 |
| 105.94 | 107.50 | 109.06 | 110.63 | 112.19 | 113.75 | 115.31 | 116.88 | 118.44 |
| 104.82 | 106.43 | 108.04 | 109.64 | 111.25 | 112.86 | 114.46 | 116.07 | 117.68 |
| 103.71 | 105.36 | 107.01 | 108.66 | 110.31 | 111.96 | 113.62 | 115.27 | 116.92 |
| 102.59 | 104.29 | 105.98 | 107.68 | 109.38 | 111.07 | 112.77 | 114.46 | 116.16 |
| 101.47 | 103.21 | 104.96 | 106.70 | 108.44 | 110.18 | 111.92 | 113.66 | 115.40 |
| 100.36 | 102.14 | 103.93 | 105.71 | 107.50 | 109.29 | 111.07 | 112.86 | 114.64 |
| 100.37 | 102.10 | 103.83 | 105.55 | 107.28 | 109.01 | 110.74 | 112.46 | 114.19 |
| 100.38 | 102.05 | 103.72 | 105.39 | 107.06 | 108.73 | 110.40 | 112.07 | 113.74 |
| 100.40 | 102.01 | 103.62 | 105.23 | 106.84 | 108.46 | 110.07 | 111.68 | 113.29 |
| 100.41 | 101.96 | 103.52 | 105.07 | 106.63 | 108.18 | 109.73 | 111.29 | 112.84 |
| 100.42 | 101.92 | 103.42 | 104.91 | 106.41 | 107.90 | 109.40 | 110.89 | 112.39 |
| 100.44 | 101.88 | 103.31 | 104.75 | 106.19 | 107.63 | 109.06 | 110.50 | 111.94 |
| 100.07 | 101.43 | 102.79 | 104.14 | 105.50 | 106.86 | 108.21 | 109.57 | 110.93 |
| 100.46 | 101.79 | 103.11 | 104.43 | 105.75 | 107.07 | 108.39 | 109.71 | 111.04 |
| 97.93 | 99.20 | 100.46 | 101.73 | 103.00 | 104.27 | 105.54 | 106.80 | 108.07 |

FIG. 7(Cont.)

| | | | | | | | |
|---|---|---|---|---|---|---|---|
| 114.64 | 116.07 | 117.50 | 116.07 | 114.64 | 113.21 | 111.79 | 110.36 | 108.93 |
| 115.89 | 117.32 | 118.75 | 117.32 | 115.89 | 114.46 | 113.04 | 111.61 | 110.18 |
| 117.14 | 118.57 | 120.00 | 118.57 | 117.14 | 115.71 | 114.29 | 112.86 | 111.43 |
| 118.39 | 119.82 | 121.25 | 119.82 | 118.39 | 116.96 | 115.54 | 114.11 | 112.68 |
| 119.64 | 121.07 | 122.50 | 121.07 | 119.64 | 118.21 | 116.79 | 115.36 | 113.93 |
| 120.89 | 122.32 | 123.75 | 122.32 | 120.89 | 119.46 | 118.04 | 116.61 | 115.18 |
| 122.14 | 123.57 | 125.00 | 123.57 | 122.14 | 120.71 | 119.29 | 117.86 | 116.43 |
| 121.43 | 122.90 | 124.38 | 122.90 | 121.43 | 119.96 | 118.48 | 117.01 | 115.54 |
| 120.71 | 122.23 | 123.75 | 122.23 | 120.71 | 119.20 | 117.68 | 116.16 | 114.64 |
| 120.00 | 121.56 | 123.13 | 121.56 | 120.00 | 118.44 | 116.88 | 115.31 | 113.75 |
| 119.29 | 120.89 | 122.50 | 120.89 | 119.29 | 117.68 | 116.07 | 114.46 | 112.86 |
| 118.57 | 120.22 | 121.88 | 120.22 | 118.57 | 116.92 | 115.27 | 113.62 | 111.96 |
| 117.86 | 119.55 | 121.25 | 119.55 | 117.86 | 116.16 | 114.46 | 112.77 | 111.07 |
| 117.14 | 118.88 | 120.63 | 118.88 | 117.14 | 115.40 | 113.66 | 111.92 | 110.18 |
| 116.43 | 118.21 | 120.00 | 118.21 | 116.43 | 114.64 | 112.86 | 111.07 | 109.29 |
| 115.92 | 117.65 | 119.38 | 117.65 | 115.92 | 114.19 | 112.46 | 110.74 | 109.01 |
| 115.41 | 117.08 | 118.75 | 117.08 | 115.41 | 113.74 | 112.07 | 110.40 | 108.73 |
| 114.90 | 116.51 | 118.13 | 116.51 | 114.90 | 113.29 | 111.68 | 110.07 | 108.46 |
| 114.39 | 115.95 | 117.50 | 115.95 | 114.39 | 112.84 | 111.29 | 109.73 | 108.18 |
| 113.88 | 115.38 | 116.88 | 115.38 | 113.88 | 112.39 | 110.89 | 109.40 | 107.90 |
| 113.38 | 114.81 | 116.25 | 114.81 | 113.38 | 111.94 | 110.50 | 109.06 | 107.63 |
| 112.29 | 113.64 | 115.63 | 113.64 | 112.29 | 110.93 | 109.57 | 108.21 | 106.86 |
| 112.36 | 113.68 | 115.00 | 113.68 | 112.36 | 111.04 | 109.71 | 108.39 | 107.07 |
| 109.34 | 110.61 | 111.88 | 110.61 | 109.34 | 108.07 | 106.80 | 105.54 | 104.27 |

FIG. 7(Cont.)

| 107.50 | 106.07 | 104.64 | 103.21 | 101.79 | 100.36 | 98.93 | 97.50 | 96.07 |
|---|---|---|---|---|---|---|---|---|
| 108.75 | 107.32 | 105.89 | 104.46 | 103.04 | 101.61 | 100.18 | 98.75 | 97.32 |
| 110.00 | 108.57 | 107.14 | 105.71 | 104.29 | 102.86 | 101.43 | 100.00 | 98.57 |
| 111.25 | 109.82 | 108.39 | 106.96 | 105.54 | 104.11 | 102.68 | 101.25 | 99.82 |
| 112.50 | 111.07 | 109.64 | 108.21 | 106.79 | 105.36 | 103.93 | 102.50 | 101.07 |
| 113.75 | 112.32 | 110.89 | 109.46 | 108.04 | 106.61 | 105.18 | 103.75 | 102.32 |
| 115.00 | 113.57 | 112.14 | 110.71 | 109.29 | 107.86 | 106.43 | 105.00 | 103.57 |
| 114.06 | 112.59 | 111.12 | 109.64 | 108.17 | 106.70 | 105.22 | 103.75 | 102.28 |
| 113.13 | 111.61 | 110.09 | 108.57 | 107.05 | 105.54 | 104.02 | 102.50 | 100.98 |
| 112.19 | 110.63 | 109.06 | 107.50 | 105.94 | 104.38 | 102.81 | 101.25 | 99.69 |
| 111.25 | 109.64 | 108.04 | 106.43 | 104.82 | 103.21 | 101.61 | 100.00 | 98.39 |
| 110.31 | 108.66 | 107.01 | 105.36 | 103.71 | 102.05 | 100.40 | 98.75 | 97.10 |
| 109.38 | 107.68 | 105.98 | 104.29 | 102.59 | 100.89 | 99.20 | 97.50 | 95.80 |
| 108.44 | 106.70 | 104.96 | 103.21 | 101.47 | 99.73 | 97.99 | 96.25 | 94.51 |
| 107.50 | 105.71 | 103.93 | 102.14 | 100.36 | 98.57 | 96.79 | 95.00 | 93.21 |
| 107.28 | 105.55 | 103.83 | 102.10 | 100.37 | 98.64 | 96.92 | 95.19 | 93.46 |
| 107.06 | 105.39 | 103.72 | 102.05 | 100.38 | 98.71 | 97.04 | 95.38 | 93.71 |
| 106.84 | 105.23 | 103.62 | 102.01 | 100.40 | 98.79 | 97.17 | 95.56 | 93.95 |
| 106.63 | 105.07 | 103.52 | 101.96 | 100.41 | 98.86 | 97.30 | 95.75 | 94.20 |
| 106.41 | 104.91 | 103.42 | 101.92 | 100.42 | 98.93 | 97.43 | 95.94 | 94.44 |
| 106.19 | 104.75 | 103.31 | 101.88 | 100.44 | 99.00 | 97.56 | 96.13 | 94.69 |
| 105.50 | 104.14 | 102.79 | 101.43 | 100.07 | 98.71 | 97.36 | 96.00 | 94.64 |
| 105.75 | 104.43 | 103.11 | 101.79 | 100.46 | 99.14 | 97.82 | 96.50 | 95.18 |
| 103.00 | 101.73 | 100.46 | 99.20 | 97.93 | 96.66 | 95.39 | 94.12 | 92.86 |

FIG. 7(Cont.)

| 94.64 | 93.21 | 91.79 | 90.36 | 88.93 | 87.50 | 86.07 | 84.64 | 83.21 |
|---|---|---|---|---|---|---|---|---|
| 95.89 | 94.46 | 93.04 | 91.61 | 90.18 | 88.75 | 87.32 | 85.89 | 84.46 |
| 97.14 | 95.71 | 94.29 | 92.86 | 91.43 | 90.00 | 88.57 | 87.14 | 85.71 |
| 98.39 | 96.96 | 95.54 | 94.11 | 92.68 | 91.25 | 89.82 | 88.39 | 86.96 |
| 99.64 | 98.21 | 96.79 | 95.36 | 93.93 | 92.50 | 91.07 | 89.64 | 88.21 |
| 100.89 | 99.46 | 98.04 | 96.61 | 95.18 | 93.75 | 92.32 | 90.89 | 89.46 |
| 102.14 | 100.71 | 99.29 | 97.86 | 96.43 | 95.00 | 93.57 | 92.14 | 90.71 |
| 100.80 | 99.33 | 97.86 | 96.38 | 94.91 | 93.44 | 91.96 | 90.49 | 89.02 |
| 99.46 | 97.95 | 96.43 | 94.91 | 93.39 | 91.88 | 90.36 | 88.84 | 87.32 |
| 98.13 | 96.56 | 95.00 | 93.44 | 91.88 | 90.31 | 88.75 | 87.19 | 85.63 |
| 96.79 | 95.18 | 93.57 | 91.96 | 90.36 | 88.75 | 87.14 | 85.54 | 83.93 |
| 95.45 | 93.79 | 92.14 | 90.49 | 88.84 | 87.19 | 85.54 | 83.88 | 82.23 |
| 94.11 | 92.41 | 90.71 | 89.02 | 87.32 | 85.63 | 83.93 | 82.23 | 80.54 |
| 92.77 | 91.03 | 89.29 | 87.54 | 85.80 | 84.06 | 82.32 | 80.58 | 78.84 |
| 91.43 | 89.64 | 87.86 | 86.07 | 84.29 | 82.50 | 80.71 | 78.93 | 77.14 |
| 91.73 | 90.00 | 88.28 | 86.55 | 84.82 | 83.09 | 81.37 | 79.64 | 77.91 |
| 92.04 | 90.37 | 88.70 | 87.03 | 85.36 | 83.69 | 82.02 | 80.35 | 78.68 |
| 92.34 | 90.73 | 89.12 | 87.50 | 85.89 | 84.28 | 82.67 | 81.06 | 79.45 |
| 92.64 | 91.09 | 89.54 | 87.98 | 86.43 | 84.88 | 83.32 | 81.77 | 80.21 |
| 92.95 | 91.45 | 89.96 | 88.46 | 86.96 | 85.47 | 83.97 | 82.48 | 80.98 |
| 93.25 | 91.81 | 90.38 | 88.94 | 87.50 | 86.06 | 84.63 | 83.19 | 81.75 |
| 93.29 | 91.93 | 90.57 | 89.21 | 87.86 | 86.50 | 85.14 | 83.79 | 82.43 |
| 93.86 | 92.54 | 91.21 | 89.89 | 88.57 | 87.25 | 85.93 | 84.61 | 83.29 |
| 91.59 | 90.32 | 89.05 | 87.79 | 86.52 | 85.25 | 83.98 | 82.71 | 81.45 |

FIG. 7(Cont.)

| 81.79 | 80.36 | 78.93 | 77.50 | 81.25 | 85.00 | 88.75 | 92.50 | 96.25 | 100.00 |
|---|---|---|---|---|---|---|---|---|---|
| 83.04 | 81.61 | 80.18 | 78.75 | 82.29 | 85.83 | 89.38 | 92.92 | 96.46 | 100.00 |
| 84.29 | 82.86 | 81.43 | 80.00 | 83.33 | 86.67 | 90.00 | 93.33 | 96.67 | 100.00 |
| 85.54 | 84.11 | 82.68 | 81.25 | 84.38 | 87.50 | 90.63 | 93.75 | 96.88 | 100.00 |
| 86.79 | 85.36 | 83.93 | 82.50 | 85.42 | 88.33 | 91.25 | 94.17 | 97.08 | 100.00 |
| 88.04 | 86.61 | 85.18 | 83.75 | 86.46 | 89.17 | 91.88 | 94.58 | 97.29 | 100.00 |
| 89.29 | 87.86 | 86.43 | 85.00 | 87.50 | 90.00 | 92.50 | 95.00 | 97.50 | 100.00 |
| 87.54 | 86.07 | 84.60 | 83.13 | 85.94 | 88.75 | 91.56 | 94.38 | 97.19 | 100.00 |
| 85.80 | 84.29 | 82.77 | 81.25 | 83.24 | 85.23 | 87.23 | 89.22 | 91.21 | 93.20 |
| 84.06 | 82.50 | 80.94 | 79.38 | 80.55 | 81.72 | 82.89 | 84.06 | 85.23 | 86.40 |
| 82.32 | 80.71 | 79.11 | 77.50 | 77.85 | 78.20 | 78.55 | 78.90 | 79.25 | 79.60 |
| 80.58 | 78.93 | 77.28 | 75.63 | 75.15 | 74.68 | 74.21 | 73.74 | 73.27 | 72.80 |
| 78.84 | 77.14 | 75.45 | 73.75 | 72.46 | 71.17 | 69.88 | 68.58 | 67.29 | 66.00 |
| 77.10 | 75.36 | 73.62 | 71.88 | 69.76 | 67.65 | 65.54 | 63.43 | 61.31 | 59.20 |
| 75.36 | 73.57 | 71.79 | 70.00 | 67.07 | 64.13 | 61.20 | 58.27 | 55.33 | 52.40 |
| 76.18 | 74.46 | 72.73 | 71.00 | 66.77 | 62.53 | 58.30 | 54.07 | 49.83 | 45.60 |
| 77.01 | 75.34 | 73.67 | 72.00 | 66.47 | 60.93 | 55.40 | 49.87 | 44.33 | 38.80 |
| 77.83 | 76.22 | 74.61 | 73.00 | 66.17 | 59.33 | 52.50 | 45.67 | 38.83 | 32.00 |
| 78.66 | 77.11 | 75.55 | 74.00 | 67.00 | 60.00 | 53.00 | 46.00 | 39.00 | 32.00 |
| 79.49 | 77.99 | 76.50 | 75.00 | 67.83 | 60.67 | 53.50 | 46.33 | 39.17 | 32.00 |
| 80.31 | 78.88 | 77.44 | 76.00 | 68.67 | 61.33 | 54.00 | 46.67 | 39.33 | 32.00 |
| 81.07 | 79.71 | 78.36 | 77.00 | 69.50 | 62.00 | 54.50 | 47.00 | 39.50 | 32.00 |
| 81.96 | 80.64 | 79.32 | 78.00 | 70.33 | 62.67 | 55.00 | 47.33 | 39.67 | 32.00 |
| 80.18 | 78.91 | 77.64 | 76.38 | 68.98 | 61.58 | 54.19 | 46.79 | 39.40 | 32.00 |

FIG. 7(Cont.)

| | | | |
|---|---|---|---|
| 48 | | | -7.13 |
| 49 | | | -6.85 |
| 50 | | | -6.58 |
| 51 | | | -6.31 |
| 52 | | | -6.04 |
| 53 | | | -5.77 |
| 54 | 0.75 | 1.25 | -5.50 |
| 55 | | | -5.38 |
| 56 | | | -5.25 |
| 57 | | | -5.13 |
| 58 | | | -5.00 |
| 59 | | | -4.88 |
| 60 | | | -4.75 |
| 61 | | | -4.63 |
| 62 | 0.38 | 1.13 | -4.50 |
| 63 | | | -4.44 |
| 64 | | | -4.38 |
| 65 | | | -4.31 |
| 66 | | | -4.25 |
| 67 | | | -4.19 |

FIG. 7(Cont.)

|  |  |  |  |  |  |  |
|---|---|---|---|---|---|---|
|  | -1.21 | 32.00 | 39.13 | 46.25 | 53.38 | 60.50 |
|  | -1.16 | 32.00 | 38.85 | 45.71 | 52.56 | 59.42 |
|  | -1.11 | 32.00 | 38.58 | 45.17 | 51.75 | 58.33 |
|  | -1.05 | 32.00 | 38.31 | 44.63 | 50.94 | 57.25 |
|  | -1.00 | 32.00 | 38.04 | 44.08 | 50.13 | 56.17 |
|  | -0.95 | 32.00 | 37.77 | 43.54 | 49.31 | 55.08 |
|  | -0.89 | 32.00 | 37.50 | 43.00 | 48.50 | 54.00 |
|  | -0.88 | 32.00 | 37.38 | 42.75 | 48.13 | 53.50 |
|  | -0.86 | 32.00 | 37.25 | 42.50 | 47.75 | 53.00 |
|  | -0.84 | 32.00 | 37.13 | 42.25 | 47.38 | 52.50 |
|  | -0.82 | 32.00 | 37.00 | 42.00 | 47.00 | 52.00 |
|  | -0.80 | 32.00 | 36.88 | 41.75 | 46.63 | 51.50 |
|  | -0.79 | 32.00 | 36.75 | 41.50 | 46.25 | 51.00 |
|  | -0.77 | 32.00 | 36.63 | 41.25 | 45.88 | 50.50 |
|  | -0.75 | 32.00 | 36.50 | 41.00 | 45.50 | 50.00 |
|  | -0.72 | 32.00 | 36.44 | 40.88 | 45.31 | 49.75 |
|  | -0.70 | 32.00 | 36.38 | 40.75 | 45.13 | 49.50 |
|  | -0.67 | 32.00 | 36.31 | 40.63 | 44.94 | 49.25 |
|  | -0.64 | 32.00 | 36.25 | 40.50 | 44.75 | 49.00 |
|  | -0.62 | 32.00 | 36.19 | 40.38 | 44.56 | 48.75 |

FIG. 7(Cont.)

| 67.63 | 74.75 | 75.96 | 77.18 | 78.39 | 79.61 | 80.82 | 82.04 | 83.25 |
|---|---|---|---|---|---|---|---|---|
| 66.27 | 73.13 | 74.29 | 75.45 | 76.61 | 77.77 | 78.93 | 80.09 | 81.25 |
| 64.92 | 71.50 | 72.61 | 73.71 | 74.82 | 75.93 | 77.04 | 78.14 | 79.25 |
| 63.56 | 69.88 | 70.93 | 71.98 | 73.04 | 74.09 | 75.14 | 76.20 | 77.25 |
| 62.21 | 68.25 | 69.25 | 70.25 | 71.25 | 72.25 | 73.25 | 74.25 | 75.25 |
| 60.85 | 66.63 | 67.57 | 68.52 | 69.46 | 70.41 | 71.36 | 72.30 | 73.25 |
| 59.50 | 65.00 | 65.89 | 66.79 | 67.68 | 68.57 | 69.46 | 70.36 | 71.25 |
| 58.88 | 64.25 | 65.13 | 66.00 | 66.88 | 67.75 | 68.63 | 69.50 | 70.38 |
| 58.25 | 63.50 | 64.36 | 65.21 | 66.07 | 66.93 | 67.79 | 68.64 | 69.50 |
| 57.63 | 62.75 | 63.59 | 64.43 | 65.27 | 66.11 | 66.95 | 67.79 | 68.63 |
| 57.00 | 62.00 | 62.82 | 63.64 | 64.46 | 65.29 | 66.11 | 66.93 | 67.75 |
| 56.38 | 61.25 | 62.05 | 62.86 | 63.66 | 64.46 | 65.27 | 66.07 | 66.88 |
| 55.75 | 60.50 | 61.29 | 62.07 | 62.86 | 63.64 | 64.43 | 65.21 | 66.00 |
| 55.13 | 59.75 | 60.52 | 61.29 | 62.05 | 62.82 | 63.59 | 64.36 | 65.13 |
| 54.50 | 59.00 | 59.75 | 60.50 | 61.25 | 62.00 | 62.75 | 63.50 | 64.25 |
| 54.19 | 58.63 | 59.35 | 60.07 | 60.79 | 61.52 | 62.24 | 62.96 | 63.69 |
| 53.88 | 58.25 | 58.95 | 59.64 | 60.34 | 61.04 | 61.73 | 62.43 | 63.13 |
| 53.56 | 57.88 | 58.54 | 59.21 | 59.88 | 60.55 | 61.22 | 61.89 | 62.56 |
| 53.25 | 57.50 | 58.14 | 58.79 | 59.43 | 60.07 | 60.71 | 61.36 | 62.00 |
| 52.94 | 57.13 | 57.74 | 58.36 | 58.97 | 59.59 | 60.21 | 60.82 | 61.44 |

FIG. 7(Cont.)

| 84.46 | 85.68 | 86.89 | 88.11 | 89.32 | 90.54 | 91.75 | 92.96 | 94.18 |
|---|---|---|---|---|---|---|---|---|
| 82.41 | 83.57 | 84.73 | 85.89 | 87.05 | 88.21 | 89.38 | 90.54 | 91.70 |
| 80.36 | 81.46 | 82.57 | 83.68 | 84.79 | 85.89 | 87.00 | 88.11 | 89.21 |
| 78.30 | 79.36 | 80.41 | 81.46 | 82.52 | 83.57 | 84.63 | 85.68 | 86.73 |
| 76.25 | 77.25 | 78.25 | 79.25 | 80.25 | 81.25 | 82.25 | 83.25 | 84.25 |
| 74.20 | 75.14 | 76.09 | 77.04 | 77.98 | 78.93 | 79.88 | 80.82 | 81.77 |
| 72.14 | 73.04 | 73.93 | 74.82 | 75.71 | 76.61 | 77.50 | 78.39 | 79.29 |
| 71.25 | 72.13 | 73.00 | 73.88 | 74.75 | 75.63 | 76.50 | 77.38 | 78.25 |
| 70.36 | 71.21 | 72.07 | 72.93 | 73.79 | 74.64 | 75.50 | 76.36 | 77.21 |
| 69.46 | 70.30 | 71.14 | 71.98 | 72.82 | 73.66 | 74.50 | 75.34 | 76.18 |
| 68.57 | 69.39 | 70.21 | 71.04 | 71.86 | 72.68 | 73.50 | 74.32 | 75.14 |
| 67.68 | 68.48 | 69.29 | 70.09 | 70.89 | 71.70 | 72.50 | 73.30 | 74.11 |
| 66.79 | 67.57 | 68.36 | 69.14 | 69.93 | 70.71 | 71.50 | 72.29 | 73.07 |
| 65.89 | 66.66 | 67.43 | 68.20 | 68.96 | 69.73 | 70.50 | 71.27 | 72.04 |
| 65.00 | 65.75 | 66.50 | 67.25 | 68.00 | 68.75 | 69.50 | 70.25 | 71.00 |
| 64.41 | 65.13 | 65.86 | 66.58 | 67.30 | 68.03 | 68.75 | 69.47 | 70.20 |
| 63.82 | 64.52 | 65.21 | 65.91 | 66.61 | 67.30 | 68.00 | 68.70 | 69.39 |
| 63.23 | 63.90 | 64.57 | 65.24 | 65.91 | 66.58 | 67.25 | 67.92 | 68.59 |
| 62.64 | 63.29 | 63.93 | 64.57 | 65.21 | 65.86 | 66.50 | 67.14 | 67.79 |
| 62.05 | 62.67 | 63.29 | 63.90 | 64.52 | 65.13 | 65.75 | 66.37 | 66.98 |

FIG. 7(Cont.)

| 95.39 | 96.61 | 97.82 | 99.04 | 100.25 | 101.46 | 102.68 | 103.89 | 105.11 |
|---|---|---|---|---|---|---|---|---|
| 92.86 | 94.02 | 95.18 | 96.34 | 97.50 | 98.66 | 99.82 | 100.98 | 102.14 |
| 90.32 | 91.43 | 92.54 | 93.64 | 94.75 | 95.86 | 96.96 | 98.07 | 99.18 |
| 87.79 | 88.84 | 89.89 | 90.95 | 92.00 | 93.05 | 94.11 | 95.16 | 96.21 |
| 85.25 | 86.25 | 87.25 | 88.25 | 89.25 | 90.25 | 91.25 | 92.25 | 93.25 |
| 82.71 | 83.66 | 84.61 | 85.55 | 86.50 | 87.45 | 88.39 | 89.34 | 90.29 |
| 80.18 | 81.07 | 81.96 | 82.86 | 83.75 | 84.64 | 85.54 | 86.43 | 87.32 |
| 79.13 | 80.00 | 80.88 | 81.75 | 82.63 | 83.50 | 84.38 | 85.25 | 86.13 |
| 78.07 | 78.93 | 79.79 | 80.64 | 81.50 | 82.36 | 83.21 | 84.07 | 84.93 |
| 77.02 | 77.86 | 78.70 | 79.54 | 80.37 | 81.21 | 82.05 | 82.89 | 83.73 |
| 75.96 | 76.79 | 77.61 | 78.43 | 79.25 | 80.07 | 80.89 | 81.71 | 82.54 |
| 74.91 | 75.71 | 76.52 | 77.32 | 78.13 | 78.93 | 79.73 | 80.54 | 81.34 |
| 73.86 | 74.64 | 75.43 | 76.21 | 77.00 | 77.79 | 78.57 | 79.36 | 80.14 |
| 72.80 | 73.57 | 74.34 | 75.11 | 75.88 | 76.64 | 77.41 | 78.18 | 78.95 |
| 71.75 | 72.50 | 73.25 | 74.00 | 74.75 | 75.50 | 76.25 | 77.00 | 77.75 |
| 70.92 | 71.64 | 72.37 | 73.09 | 73.81 | 74.54 | 75.26 | 75.98 | 76.71 |
| 70.09 | 70.79 | 71.48 | 72.18 | 72.88 | 73.57 | 74.27 | 74.96 | 75.66 |
| 69.26 | 69.93 | 70.60 | 71.27 | 71.94 | 72.61 | 73.28 | 73.95 | 74.62 |
| 68.43 | 69.07 | 69.71 | 70.36 | 71.00 | 71.64 | 72.29 | 72.93 | 73.57 |
| 67.60 | 68.21 | 68.83 | 69.45 | 70.06 | 70.68 | 71.29 | 71.91 | 72.53 |

FIG. 7(Cont.)

| 106.32 | 107.54 | 108.75 | 107.54 | 106.32 | 105.11 | 103.89 | 102.68 | 101.46 |
|---|---|---|---|---|---|---|---|---|
| 103.30 | 104.46 | 105.63 | 104.46 | 103.30 | 102.14 | 100.98 | 99.82 | 98.66 |
| 100.29 | 101.39 | 102.50 | 101.39 | 100.29 | 99.18 | 98.07 | 96.96 | 95.86 |
| 97.27 | 98.32 | 99.38 | 98.32 | 97.27 | 96.21 | 95.16 | 94.11 | 93.05 |
| 94.25 | 95.25 | 96.25 | 95.25 | 94.25 | 93.25 | 92.25 | 91.25 | 90.25 |
| 91.23 | 92.18 | 93.13 | 92.18 | 91.23 | 90.29 | 89.34 | 88.39 | 87.45 |
| 88.21 | 89.11 | 90.00 | 89.11 | 88.21 | 87.32 | 86.43 | 85.54 | 84.64 |
| 87.00 | 87.88 | 88.75 | 87.88 | 87.00 | 86.13 | 85.25 | 84.38 | 83.50 |
| 85.79 | 86.64 | 87.50 | 86.64 | 85.79 | 84.93 | 84.07 | 83.21 | 82.36 |
| 84.57 | 85.41 | 86.25 | 85.41 | 84.57 | 83.73 | 82.89 | 82.05 | 81.21 |
| 83.36 | 84.18 | 85.00 | 84.18 | 83.36 | 82.54 | 81.71 | 80.89 | 80.07 |
| 82.14 | 82.95 | 83.75 | 82.95 | 82.14 | 81.34 | 80.54 | 79.73 | 78.93 |
| 80.93 | 81.71 | 82.50 | 81.71 | 80.93 | 80.14 | 79.36 | 78.57 | 77.79 |
| 79.71 | 80.48 | 81.25 | 80.48 | 79.71 | 78.95 | 78.18 | 77.41 | 76.64 |
| 78.50 | 79.25 | 80.00 | 79.25 | 78.50 | 77.75 | 77.00 | 76.25 | 75.50 |
| 77.43 | 78.15 | 78.88 | 78.15 | 77.43 | 76.71 | 75.98 | 75.26 | 74.54 |
| 76.36 | 77.05 | 77.75 | 77.05 | 76.36 | 75.66 | 74.96 | 74.27 | 73.57 |
| 75.29 | 75.96 | 76.63 | 75.96 | 75.29 | 74.62 | 73.95 | 73.28 | 72.61 |
| 74.21 | 74.86 | 75.50 | 74.86 | 74.21 | 73.57 | 72.93 | 72.29 | 71.64 |
| 73.14 | 73.76 | 74.38 | 73.76 | 73.14 | 72.53 | 71.91 | 71.29 | 70.68 |

FIG. 7(Cont.)

| | | | | | | | |
|---|---|---|---|---|---|---|---|
| 100.25 | 99.04 | 97.82 | 96.61 | 95.39 | 94.18 | 92.96 | 91.75 | 90.54 |
| 97.50 | 96.34 | 95.18 | 94.02 | 92.86 | 91.70 | 90.54 | 89.38 | 88.21 |
| 94.75 | 93.64 | 92.54 | 91.43 | 90.32 | 89.21 | 88.11 | 87.00 | 85.89 |
| 92.00 | 90.95 | 89.89 | 88.84 | 87.79 | 86.73 | 85.68 | 84.63 | 83.57 |
| 89.25 | 88.25 | 87.25 | 86.25 | 85.25 | 84.25 | 83.25 | 82.25 | 81.25 |
| 86.50 | 85.55 | 84.61 | 83.66 | 82.71 | 81.77 | 80.82 | 79.88 | 78.93 |
| 83.75 | 82.86 | 81.96 | 81.07 | 80.18 | 79.29 | 78.39 | 77.50 | 76.61 |
| 82.63 | 81.75 | 80.88 | 80.00 | 79.13 | 78.25 | 77.38 | 76.50 | 75.63 |
| 81.50 | 80.64 | 79.79 | 78.93 | 78.07 | 77.21 | 76.36 | 75.50 | 74.64 |
| 80.37 | 79.54 | 78.70 | 77.86 | 77.02 | 76.18 | 75.34 | 74.50 | 73.66 |
| 79.25 | 78.43 | 77.61 | 76.79 | 75.96 | 75.14 | 74.32 | 73.50 | 72.68 |
| 78.13 | 77.32 | 76.52 | 75.71 | 74.91 | 74.11 | 73.30 | 72.50 | 71.70 |
| 77.00 | 76.21 | 75.43 | 74.64 | 73.86 | 73.07 | 72.29 | 71.50 | 70.71 |
| 75.88 | 75.11 | 74.34 | 73.57 | 72.80 | 72.04 | 71.27 | 70.50 | 69.73 |
| 74.75 | 74.00 | 73.25 | 72.50 | 71.75 | 71.00 | 70.25 | 69.50 | 68.75 |
| 73.81 | 73.09 | 72.37 | 71.64 | 70.92 | 70.20 | 69.47 | 68.75 | 68.03 |
| 72.88 | 72.18 | 71.48 | 70.79 | 70.09 | 69.39 | 68.70 | 68.00 | 67.30 |
| 71.94 | 71.27 | 70.60 | 69.93 | 69.26 | 68.59 | 67.92 | 67.25 | 66.58 |
| 71.00 | 70.36 | 69.71 | 69.07 | 68.43 | 67.79 | 67.14 | 66.50 | 65.86 |
| 70.06 | 69.45 | 68.83 | 68.21 | 67.60 | 66.98 | 66.37 | 65.75 | 65.13 |

FIG. 7(Cont.)

| 89.32 | 88.11 | 86.89 | 85.68 | 84.46 | 83.25 | 82.04 | 80.82 | 79.61 |
|-------|-------|-------|-------|-------|-------|-------|-------|-------|
| 87.05 | 85.89 | 84.73 | 83.57 | 82.41 | 81.25 | 80.09 | 78.93 | 77.77 |
| 84.79 | 83.68 | 82.57 | 81.46 | 80.36 | 79.25 | 78.14 | 77.04 | 75.93 |
| 82.52 | 81.46 | 80.41 | 79.36 | 78.30 | 77.25 | 76.20 | 75.14 | 74.09 |
| 80.25 | 79.25 | 78.25 | 77.25 | 76.25 | 75.25 | 74.25 | 73.25 | 72.25 |
| 77.98 | 77.04 | 76.09 | 75.14 | 74.20 | 73.25 | 72.30 | 71.36 | 70.41 |
| 75.71 | 74.82 | 73.93 | 73.04 | 72.14 | 71.25 | 70.36 | 69.46 | 68.57 |
| 74.75 | 73.88 | 73.00 | 72.13 | 71.25 | 70.38 | 69.50 | 68.63 | 67.75 |
| 73.79 | 72.93 | 72.07 | 71.21 | 70.36 | 69.50 | 68.64 | 67.79 | 66.93 |
| 72.82 | 71.98 | 71.14 | 70.30 | 69.46 | 68.63 | 67.79 | 66.95 | 66.11 |
| 71.86 | 71.04 | 70.21 | 69.39 | 68.57 | 67.75 | 66.93 | 66.11 | 65.29 |
| 70.89 | 70.09 | 69.29 | 68.48 | 67.68 | 66.88 | 66.07 | 65.27 | 64.46 |
| 69.93 | 69.14 | 68.36 | 67.57 | 66.79 | 66.00 | 65.21 | 64.43 | 63.64 |
| 68.96 | 68.20 | 67.43 | 66.66 | 65.89 | 65.13 | 64.36 | 63.59 | 62.82 |
| 68.00 | 67.25 | 66.50 | 65.75 | 65.00 | 64.25 | 63.50 | 62.75 | 62.00 |
| 67.30 | 66.58 | 65.86 | 65.13 | 64.41 | 63.69 | 62.96 | 62.24 | 61.52 |
| 66.61 | 65.91 | 65.21 | 64.52 | 63.82 | 63.13 | 62.43 | 61.73 | 61.04 |
| 65.91 | 65.24 | 64.57 | 63.90 | 63.23 | 62.56 | 61.89 | 61.22 | 60.55 |
| 65.21 | 64.57 | 63.93 | 63.29 | 62.64 | 62.00 | 61.36 | 60.71 | 60.07 |
| 64.52 | 63.90 | 63.29 | 62.67 | 62.05 | 61.44 | 60.82 | 60.21 | 59.59 |

FIG. 7(Cont.)

| 78.39 | 77.18 | 75.96 | 74.75 | 67.63 | 60.50 | 53.38 | 46.25 | 39.13 | 32.00 |
|---|---|---|---|---|---|---|---|---|---|
| 76.61 | 75.45 | 74.29 | 73.13 | 66.27 | 59.42 | 52.56 | 45.71 | 38.85 | 32.00 |
| 74.82 | 73.71 | 72.61 | 71.50 | 64.92 | 58.33 | 51.75 | 45.17 | 38.58 | 32.00 |
| 73.04 | 71.98 | 70.93 | 69.88 | 63.56 | 57.25 | 50.94 | 44.63 | 38.31 | 32.00 |
| 71.25 | 70.25 | 69.25 | 68.25 | 62.21 | 56.17 | 50.13 | 44.08 | 38.04 | 32.00 |
| 69.46 | 68.52 | 67.57 | 66.63 | 60.85 | 55.08 | 49.31 | 43.54 | 37.77 | 32.00 |
| 67.68 | 66.79 | 65.89 | 65.00 | 59.50 | 54.00 | 48.50 | 43.00 | 37.50 | 32.00 |
| 66.88 | 66.00 | 65.13 | 64.25 | 58.88 | 53.50 | 48.13 | 42.75 | 37.38 | 32.00 |
| 66.07 | 65.21 | 64.36 | 63.50 | 58.25 | 53.00 | 47.75 | 42.50 | 37.25 | 32.00 |
| 65.27 | 64.43 | 63.59 | 62.75 | 57.63 | 52.50 | 47.38 | 42.25 | 37.13 | 32.00 |
| 64.46 | 63.64 | 62.82 | 62.00 | 57.00 | 52.00 | 47.00 | 42.00 | 37.00 | 32.00 |
| 63.66 | 62.86 | 62.05 | 61.25 | 56.38 | 51.50 | 46.63 | 41.75 | 36.88 | 32.00 |
| 62.86 | 62.07 | 61.29 | 60.50 | 55.75 | 51.00 | 46.25 | 41.50 | 36.75 | 32.00 |
| 62.05 | 61.29 | 60.52 | 59.75 | 55.13 | 50.50 | 45.88 | 41.25 | 36.63 | 32.00 |
| 61.25 | 60.50 | 59.75 | 59.00 | 54.50 | 50.00 | 45.50 | 41.00 | 36.50 | 32.00 |
| 60.79 | 60.07 | 59.35 | 58.63 | 54.19 | 49.75 | 45.31 | 40.88 | 36.44 | 32.00 |
| 60.34 | 59.64 | 58.95 | 58.25 | 53.88 | 49.50 | 45.13 | 40.75 | 36.38 | 32.00 |
| 59.88 | 59.21 | 58.54 | 57.88 | 53.56 | 49.25 | 44.94 | 40.63 | 36.31 | 32.00 |
| 59.43 | 58.79 | 58.14 | 57.50 | 53.25 | 49.00 | 44.75 | 40.50 | 36.25 | 32.00 |
| 58.97 | 58.36 | 57.74 | 57.13 | 52.94 | 48.75 | 44.56 | 40.38 | 36.19 | 32.00 |

FIG. 7(Cont.)

| | | | |
|---|---|---|---|
| 68 | | | -4.13 |
| 69 | | | -4.06 |
| 70 | -0.06 | 0.38 | -4.00 |
| 71 | | | -4.01 |
| 72 | | | -4.02 |
| 73 | | | -4.03 |
| 74 | | | -4.04 |
| 75 | | | -4.05 |
| 76 | | | -4.06 |
| 77 | | | |
| 78 | | | |
| 79 | | | |
| 80 | | | |
| 81 | | | |
| 82 | | | |

FIG. 7(Cont.)

|   |   |   |   |   |   |   |
|---|---|---|---|---|---|---|
|   |   | -0.59 | 32.00 | 36.13 | 40.25 | 44.38 | 48.50 |
|   |   | -0.56 | 32.00 | 36.06 | 40.13 | 44.19 | 48.25 |
|   |   | -0.54 | 32.00 | 36.00 | 40.00 | 44.00 | 48.00 |
|   |   | -0.50 | 32.00 | 36.01 | 40.02 | 44.03 | 48.04 |
|   |   | -0.48 | 32.00 | 36.02 | 40.04 | 44.06 | 48.08 |
|   |   | -0.47 | 32.00 | 36.03 | 40.06 | 44.09 | 48.13 |
|   |   | -0.45 | 32.00 | 36.04 | 40.08 | 44.13 | 48.17 |
|   |   | -0.44 | 32.00 | 36.05 | 40.10 | 44.16 | 48.21 |
|   |   | -0.42 | 32.00 | 36.06 | 40.13 | 44.19 | 48.25 |
|   |   | -0.40 | 32.06 | 36.13 | 40.19 | 44.25 | 48.31 |
|   |   | -0.41 | 32.13 | 36.19 | 40.25 | 44.31 | 48.38 |
|   |   | -0.40 | 32.19 | 36.25 | 40.31 | 44.38 | 48.44 |
|   |   | -0.38 | 32.25 | 36.31 | 40.38 | 44.44 | 48.50 |
|   |   | -0.36 | 32.31 | 36.38 | 40.44 | 44.50 | 48.56 |
|   |   | -0.35 | 32.38 | 36.44 | 40.50 | 44.56 | 48.63 |

FIG. 7(Cont.)

| 52.63 | 56.75 | 57.34 | 57.93 | 58.52 | 59.11 | 59.70 | 60.29 | 60.88 |
|---|---|---|---|---|---|---|---|---|
| 52.31 | 56.38 | 56.94 | 57.50 | 58.06 | 58.63 | 59.19 | 59.75 | 60.31 |
| 52.00 | 56.00 | 56.54 | 57.07 | 57.61 | 58.14 | 58.68 | 59.21 | 59.75 |
| 52.05 | 56.06 | 56.56 | 57.06 | 57.56 | 58.05 | 58.55 | 59.05 | 59.55 |
| 52.10 | 56.13 | 56.61 | 57.09 | 57.57 | 58.05 | 58.54 | 59.02 | 59.50 |
| 52.16 | 56.19 | 56.65 | 57.12 | 57.59 | 58.05 | 58.52 | 58.99 | 59.45 |
| 52.21 | 56.25 | 56.70 | 57.15 | 57.60 | 58.05 | 58.50 | 58.96 | 59.41 |
| 52.26 | 56.31 | 56.75 | 57.18 | 57.62 | 58.05 | 58.49 | 58.92 | 59.36 |
| 52.31 | 56.38 | 56.79 | 57.21 | 57.63 | 58.05 | 58.47 | 58.89 | 59.31 |
| 52.38 | 56.44 | 56.84 | 57.25 | 57.65 | 58.05 | 58.46 | 58.86 | 59.27 |
| 52.44 | 56.50 | 56.91 | 57.32 | 57.73 | 58.14 | 58.55 | 58.96 | 59.36 |
| 52.50 | 56.56 | 56.96 | 57.35 | 57.75 | 58.14 | 58.54 | 58.93 | 59.33 |
| 52.56 | 56.63 | 57.00 | 57.38 | 57.76 | 58.14 | 58.52 | 58.90 | 59.28 |
| 52.63 | 56.69 | 57.05 | 57.42 | 57.78 | 58.14 | 58.51 | 58.87 | 59.23 |
| 52.69 | 56.75 | 57.10 | 57.45 | 57.79 | 58.14 | 58.49 | 58.84 | 59.19 |

FIG. 7(Cont.)

| 61.46 | 62.05 | 62.64 | 63.23 | 63.82 | 64.41 | 65.00 | 65.59 | 66.18 |
|---|---|---|---|---|---|---|---|---|
| 60.88 | 61.44 | 62.00 | 62.56 | 63.13 | 63.69 | 64.25 | 64.81 | 65.38 |
| 60.29 | 60.82 | 61.36 | 61.89 | 62.43 | 62.96 | 63.50 | 64.04 | 64.57 |
| 60.04 | 60.54 | 61.04 | 61.54 | 62.04 | 62.53 | 63.03 | 63.53 | 64.03 |
| 59.98 | 60.46 | 60.95 | 61.43 | 61.91 | 62.39 | 62.88 | 63.36 | 63.84 |
| 59.92 | 60.39 | 60.85 | 61.32 | 61.79 | 62.25 | 62.72 | 63.19 | 63.65 |
| 59.86 | 60.31 | 60.76 | 61.21 | 61.66 | 62.11 | 62.56 | 63.01 | 63.46 |
| 59.79 | 60.23 | 60.67 | 61.10 | 61.54 | 61.97 | 62.41 | 62.84 | 63.28 |
| 59.73 | 60.15 | 60.57 | 60.99 | 61.41 | 61.83 | 62.25 | 62.67 | 63.09 |
| 59.67 | 60.07 | 60.48 | 60.88 | 61.29 | 61.69 | 62.09 | 62.50 | 62.90 |
| 59.79 | 60.20 | 60.61 | 61.02 | 61.43 | 61.84 | 62.25 | 62.66 | 63.07 |
| 59.72 | 60.12 | 60.51 | 60.91 | 61.30 | 61.70 | 62.09 | 62.49 | 62.88 |
| 59.66 | 60.04 | 60.42 | 60.80 | 61.18 | 61.56 | 61.94 | 62.32 | 62.70 |
| 59.60 | 59.96 | 60.33 | 60.69 | 61.05 | 61.42 | 61.78 | 62.15 | 62.51 |
| 59.54 | 59.88 | 60.23 | 60.58 | 60.93 | 61.28 | 61.63 | 61.97 | 62.32 |

FIG. 7(Cont.)

| 66.77 | 67.36 | 67.95 | 68.54 | 69.13 | 69.71 | 70.30 | 70.89 | 71.48 |
|---|---|---|---|---|---|---|---|---|
| 65.94 | 66.50 | 67.06 | 67.63 | 68.19 | 68.75 | 69.31 | 69.88 | 70.44 |
| 65.11 | 65.64 | 66.18 | 66.71 | 67.25 | 67.79 | 68.32 | 68.86 | 69.39 |
| 64.52 | 65.02 | 65.52 | 66.02 | 66.52 | 67.01 | 67.51 | 68.01 | 68.51 |
| 64.32 | 64.80 | 65.29 | 65.77 | 66.25 | 66.73 | 67.21 | 67.70 | 68.18 |
| 64.12 | 64.58 | 65.05 | 65.52 | 65.98 | 66.45 | 66.92 | 67.38 | 67.85 |
| 63.92 | 64.37 | 64.82 | 65.27 | 65.72 | 66.17 | 66.62 | 67.07 | 67.52 |
| 63.71 | 64.15 | 64.58 | 65.02 | 65.45 | 65.89 | 66.32 | 66.76 | 67.19 |
| 63.51 | 63.93 | 64.35 | 64.77 | 65.19 | 65.61 | 66.03 | 66.45 | 66.87 |
| 63.31 | 63.71 | 64.11 | 64.52 | 64.92 | 65.33 | 65.73 | 66.13 | 66.54 |
| 63.48 | 63.89 | 64.30 | 64.71 | 65.13 | 65.54 | 65.95 | 66.36 | 66.77 |
| 63.28 | 63.67 | 64.07 | 64.46 | 64.86 | 65.25 | 65.65 | 66.04 | 66.44 |
| 63.08 | 63.46 | 63.83 | 64.21 | 64.59 | 64.97 | 65.35 | 65.73 | 66.11 |
| 62.87 | 63.24 | 63.60 | 63.96 | 64.33 | 64.69 | 65.06 | 65.42 | 65.78 |
| 62.67 | 63.02 | 63.37 | 63.71 | 64.06 | 64.41 | 64.76 | 65.11 | 65.46 |

FIG. 7(Cont.)

| 72.07 | 72.66 | 73.25 | 72.66 | 72.07 | 71.48 | 70.89 | 70.30 | 69.71 |
|-------|-------|-------|-------|-------|-------|-------|-------|-------|
| 71.00 | 71.56 | 72.13 | 71.56 | 71.00 | 70.44 | 69.88 | 69.31 | 68.75 |
| 69.93 | 70.46 | 71.00 | 70.46 | 69.93 | 69.39 | 68.86 | 68.32 | 67.79 |
| 69.00 | 69.50 | 70.00 | 69.50 | 69.00 | 68.51 | 68.01 | 67.51 | 67.01 |
| 68.66 | 69.14 | 69.63 | 69.14 | 68.66 | 68.18 | 67.70 | 67.21 | 66.73 |
| 68.32 | 68.78 | 69.25 | 68.78 | 68.32 | 67.85 | 67.38 | 66.92 | 66.45 |
| 67.97 | 68.42 | 68.88 | 68.42 | 67.97 | 67.52 | 67.07 | 66.62 | 66.17 |
| 67.63 | 68.06 | 68.50 | 68.06 | 67.63 | 67.19 | 66.76 | 66.32 | 65.89 |
| 67.29 | 67.71 | 68.13 | 67.71 | 67.29 | 66.87 | 66.45 | 66.03 | 65.61 |
| 66.94 | 67.35 | 67.75 | 67.35 | 66.94 | 66.54 | 66.13 | 65.73 | 65.33 |
| 67.18 | 67.59 | 68.00 | 67.59 | 67.18 | 66.77 | 66.36 | 65.95 | 65.54 |
| 66.83 | 67.23 | 67.63 | 67.23 | 66.83 | 66.44 | 66.04 | 65.65 | 65.25 |
| 66.49 | 66.87 | 67.25 | 66.87 | 66.49 | 66.11 | 65.73 | 65.35 | 64.97 |
| 66.15 | 66.51 | 66.88 | 66.51 | 66.15 | 65.78 | 65.42 | 65.06 | 64.69 |
| 65.80 | 66.15 | 66.50 | 66.15 | 65.80 | 65.46 | 65.11 | 64.76 | 64.41 |

FIG. 7(Cont.)

| 69.13 | 68.54 | 67.95 | 67.36 | 66.77 | 66.18 | 65.59 | 65.00 | 64.41 |
| 68.19 | 67.63 | 67.06 | 66.50 | 65.94 | 65.38 | 64.81 | 64.25 | 63.69 |
| 67.25 | 66.71 | 66.18 | 65.64 | 65.11 | 64.57 | 64.04 | 63.50 | 62.96 |
| 66.52 | 66.02 | 65.52 | 65.02 | 64.52 | 64.03 | 63.53 | 63.03 | 62.53 |
| 66.25 | 65.77 | 65.29 | 64.80 | 64.32 | 63.84 | 63.36 | 62.88 | 62.39 |
| 65.98 | 65.52 | 65.05 | 64.58 | 64.12 | 63.65 | 63.19 | 62.72 | 62.25 |
| 65.72 | 65.27 | 64.82 | 64.37 | 63.92 | 63.46 | 63.01 | 62.56 | 62.11 |
| 65.45 | 65.02 | 64.58 | 64.15 | 63.71 | 63.28 | 62.84 | 62.41 | 61.97 |
| 65.19 | 64.77 | 64.35 | 63.93 | 63.51 | 63.09 | 62.67 | 62.25 | 61.83 |
| 64.92 | 64.52 | 64.11 | 63.71 | 63.31 | 62.90 | 62.50 | 62.09 | 61.69 |
| 65.13 | 64.71 | 64.30 | 63.89 | 63.48 | 63.07 | 62.66 | 62.25 | 61.84 |
| 64.86 | 64.46 | 64.07 | 63.67 | 63.28 | 62.88 | 62.49 | 62.09 | 61.70 |
| 64.59 | 64.21 | 63.83 | 63.46 | 63.08 | 62.70 | 62.32 | 61.94 | 61.56 |
| 64.33 | 63.96 | 63.60 | 63.24 | 62.87 | 62.51 | 62.15 | 61.78 | 61.42 |
| 64.06 | 63.71 | 63.37 | 63.02 | 62.67 | 62.32 | 61.97 | 61.63 | 61.28 |

FIG. 7(Cont.)

| 63.82 | 63.23 | 62.64 | 62.05 | 61.46 | 60.88 | 60.29 | 59.70 | 59.11 |
|---|---|---|---|---|---|---|---|---|
| 63.13 | 62.56 | 62.00 | 61.44 | 60.88 | 60.31 | 59.75 | 59.19 | 58.63 |
| 62.43 | 61.89 | 61.36 | 60.82 | 60.29 | 59.75 | 59.21 | 58.68 | 58.14 |
| 62.04 | 61.54 | 61.04 | 60.54 | 60.04 | 59.55 | 59.05 | 58.55 | 58.05 |
| 61.91 | 61.43 | 60.95 | 60.46 | 59.98 | 59.50 | 59.02 | 58.54 | 58.05 |
| 61.79 | 61.32 | 60.85 | 60.39 | 59.92 | 59.45 | 58.99 | 58.52 | 58.05 |
| 61.66 | 61.21 | 60.76 | 60.31 | 59.86 | 59.41 | 58.96 | 58.50 | 58.05 |
| 61.54 | 61.10 | 60.67 | 60.23 | 59.79 | 59.36 | 58.92 | 58.49 | 58.05 |
| 61.41 | 60.99 | 60.57 | 60.15 | 59.73 | 59.31 | 58.89 | 58.47 | 58.05 |
| 61.29 | 60.88 | 60.48 | 60.07 | 59.67 | 59.27 | 58.86 | 58.46 | 58.05 |
| 61.43 | 61.02 | 60.61 | 60.20 | 59.79 | 59.38 | 58.96 | 58.55 | 58.14 |
| 61.30 | 60.91 | 60.51 | 60.12 | 59.72 | 59.33 | 58.93 | 58.54 | 58.14 |
| 61.18 | 60.80 | 60.42 | 60.04 | 59.66 | 59.28 | 58.90 | 58.52 | 58.14 |
| 61.05 | 60.69 | 60.33 | 59.96 | 59.60 | 59.23 | 58.87 | 58.51 | 58.14 |
| 60.93 | 60.58 | 60.23 | 59.88 | 59.54 | 59.19 | 58.84 | 58.49 | 58.14 |

FIG. 7(Cont.)

| 58.52 | 57.93 | 57.34 | 56.75 | 52.63 | 48.50 | 44.38 | 40.25 | 36.13 | 32.00 |
|-------|-------|-------|-------|-------|-------|-------|-------|-------|-------|
| 58.06 | 57.50 | 56.94 | 56.38 | 52.31 | 48.25 | 44.19 | 40.13 | 36.06 | 32.00 |
| 57.61 | 57.07 | 56.54 | 56.00 | 52.00 | 48.00 | 44.00 | 40.00 | 36.00 | 32.00 |
| 57.56 | 57.05 | 56.56 | 56.06 | 52.05 | 48.04 | 44.03 | 40.02 | 36.01 | 32.00 |
| 57.57 | 57.09 | 56.61 | 56.13 | 52.10 | 48.08 | 44.06 | 40.04 | 36.02 | 32.00 |
| 57.59 | 57.12 | 56.65 | 56.19 | 52.16 | 48.13 | 44.09 | 40.06 | 36.03 | 32.00 |
| 57.60 | 57.15 | 56.70 | 56.25 | 52.21 | 48.17 | 44.13 | 40.08 | 36.04 | 32.00 |
| 57.62 | 57.18 | 56.75 | 56.31 | 52.26 | 48.21 | 44.16 | 40.10 | 36.05 | 32.00 |
| 57.63 | 57.21 | 56.79 | 56.38 | 52.31 | 48.25 | 44.19 | 40.13 | 36.06 | 32.00 |
| 57.65 | 57.25 | 56.84 | 56.44 | 52.38 | 48.31 | 44.25 | 40.19 | 36.13 | 32.06 |
| 57.73 | 57.32 | 56.91 | 56.50 | 52.44 | 48.38 | 44.31 | 40.25 | 36.19 | 32.13 |
| 57.75 | 57.35 | 56.96 | 56.56 | 52.50 | 48.44 | 44.38 | 40.31 | 36.25 | 32.19 |
| 57.76 | 57.38 | 57.00 | 56.63 | 52.56 | 48.50 | 44.44 | 40.38 | 36.31 | 32.25 |
| 57.78 | 57.42 | 57.05 | 56.69 | 52.63 | 48.56 | 44.50 | 40.44 | 36.38 | 32.31 |
| 57.79 | 57.45 | 57.10 | 56.75 | 52.69 | 48.63 | 44.56 | 40.50 | 36.44 | 32.38 |

FIG. 7

SYSTEM AND METHOD FOR MONITORING AND CONTROLLING CONDITIONS WITHIN A VESSEL

CROSS-REFERENCE TO RELATED APPLICATIONS

This application is a continuation of U.S. Ser. No. 16/545,492, filed Feb. 20, 2019, which claims priority to U.S. Provisional Patent Application Ser. No. 62/724,288 filed Aug. 29, 2018.

BACKGROUND OF THE INVENTION

The present invention relates generally to a system and method for monitoring and controlling conditions within a containment vessel. More particularly, the present invention relates to a system and method for monitoring and controlling conditions such as temperature, pressure, density, flow, chemical constituents or the like, within vessels used to store or process materials. Still more particularly, the present invention relates to a system and method which employs at least two sensor arrays positioned in a containment vessel that sense a condition within the vessel and communicate data to a computer running a three-dimensional interpolation model of the vessel to interpolate the condition data across the three-dimensional geometry of the vessel. The three-dimensional data may then be displayed on a graphical user interface in either two dimensional or three-dimensional format.

The system and method of the present invention has broad application across a wide variety of applications, including, for example oil and gas storage tanks, pipelines, or transports, chemical storage or processing vessels, pharmaceutical or biological reaction vessels, and/or alcohol fermentation, aging or storage vessels.

For purposes of illustration only, the present invention will be described with reference to fermentation vessels employed in alcoholic beverage preparation, particularly in the field of wine fermentation. Currently in the field of wine fermentation, understanding of the thermal state of the fermenter is accomplished by using one or more temperature sensors arranged in a variety of locations. Each sensor reports the temperature of only that single location. The vessel in which the fermentation occurs typically does not have a uniform or homogeneous temperature state. This is due to the multiple densities of solids and liquids, an exothermic reaction of yeast during fermentation, and the use of warming or cooling elements the vessel may have. Using spot temperature measurements only provides localized information limiting understanding of the vessels complete thermal state.

Many decisions in the process of making wine rely on the thermal states of the tank contents during the entire fermentation process. For example, the decision process for methodology, timing, and duration related to mixing the tank contents are highly influenced by understanding the thermal state within the tank at any given point in time. Similarly, biological considerations during the fermentation process must be understood as they are highly dependent upon temperature monitoring and control. For example, choices attendant to yeast selection, inoculation and interaction are highly dependent upon understanding the thermal conditions and processes within the tank.

Thus, it has been recognized that accurate modeling of a vessel's thermal state and conditions within a tank coupled with dynamic visualization of the thermal conditions within the tank, will allow for far greater control over the fermentation processes and, ultimately, improve wine quality.

As used herein the following terms have the following meanings:

The terms "container," "tank," and "vessel" are used synonymously to refer to any type of structure suitable for containing or conveying fluids, solids and particulates having an interior chamber into which the fluids, solids or particulates are introduced. The vessel may be of virtually any regular geometric shape, including cylindrical, spherical, cubic or other, preferably, regular geometric shapes. The system and method are agnostic to the geometry of the vessel.

"Must" is a term well known in the wine-making arts and is used to refer to the fluid and particulates, such as grape skins and seeds that are extracted through crushing grapes.

"Pump over" is a term well known in the wine-making arts and is used to refer to a process of moving fermenting must to the top of the fermentation tank.

"Alcohol fermentation" is a term known in the alcohol beverage making arts and refers to the process of converting sugar into alcohol compounds by yeast.

"Malolactic fermentation" is a term known in the wine-making arts and refers to the process of converting malic acid to lactic acid by bacteria.

"Thermowell" is a term known in the process engineering arts to mean a solid, nonwelded, machined tube configured to be introduced into process fluids and isolate temperature sensing devices from the process fluids. In this application, the term "thermowell" is intended to include any type of tube or housing configured to house a sensor in a process medium. In the case of temperature sensing devices and other sensing devices that may require fluid isolation, the thermowells may be sealed and isolate the devices from the process fluids, in the case of other sensing devices including but not limited to pH or pressure sensing devices, the thermowells may be open or porous exposing the sensing devices to the process fluids.

Efforts to automate control over wine fermentation exist in the prior art. One example includes a complex computer controlled multi-tank pumping system for yeast propagation control that measures yeast concentration based upon cell counting and Baume values (a hydrometer scale for measuring specific gravity of liquids). (U.S. Pat. No. 4,856,421). U.S. Pat. No. 4,711,785 describes a system which employs a temperature probe positioned external to the tank and inline in a fluid recirculating circuit to measure the fluid temperature as fluid is reinjected into the tank after being heated or cooled. Chinese Patent CN2480370 discloses a fermentation tank having a temperature sensor coupled to a tank lid which senses the temperature of the fluid and activates a heating controller and electric mixer. German Patent DE10131158 discloses a fermentation system in which density changes are measured by employing two or more pressure sensors positioned at different height positions within the fermentation tank. A temperature sensor is also employed to convert the measured density to a temperature value. The system monitors the differential pressure, converts the pressure data to temperature with reference to the temperature sensor, and correlates the pressure and temperature data to pre-determined acceptable parameters and, in conjunction with a microcomputer, controls a heat exchanger to heat or cool the fluid in the tank. German Patent DE10247654, like the previously described German Patent, employs pressure sensors to measure the density of the fermenting fluid within a tank, and also employs a display image screen, a control unit and a processing device to visualize a graphical representation of the system and its states. French Patent No. FR2743145 discloses a system for monitoring and controlling temperature in wine fermentation tanks in which a temperature probe is inserted into the "third bottom of the height of the tanks" to measure the temperature of the wines during fermentation. The temperature sensors are coupled to a voltage amplifier and to a controller that issues an alarm if the measured temperature exceeds a predetermined limit. Finally, U.S. Pat. No. 8,794,049 discloses a real-time monitoring system for wine fermentation which employs a pressure sensor external to the fermentation tank that measures increasing pressure of carbon dioxide given off during fermentation as a measurement of the fermentation process.

None of the foregoing known systems for monitoring and/or controlling fermentation in a vessel employ sensor arrays in known positions to generate data at the known positions and then using regression modeling, interpolate the data across the entire volume of the fluid within the tank.

SUMMARY OF THE INVENTION

An objective of the present invention is to provide a system and method for measuring the one of more conditions of material within a containment tank. More, particularly, it is an objective of the present invention to provide a system and method that monitors temperature and density of fluid and solids within a containment tank by positioning parallel multipoint sensors or sensor arrays within the containment tank to collect temperature and density data within the tank and algorithmically interpolate temperature and/or density data between and beyond known data points along the vertical, horizontal and circumferential or radial axes of the tank.

It is a further objective of the present invention to display the interpolated data in a numerical matrix and/or a graphical color gradient representation of the interpolated data.

It is yet a further objective of the present invention to communicate the interpolated data to a computer controller having a control logic circuit electrically coupled to one or more pumps and gates in fluid flow circuits that control i. cooling and/or heating fluid flow through thermal jackets associated with the vessel, ii. Recirculation pumps and gates communicating between upper and lower regions of the vessel to allow for circulation of fluids at the bottom of the tank into the top of the tank, and/or iii. Regulating inflow or outflow of fluid into the tank.

It is still another objective of the present invention to communicate the interpolated data, together with other data regarding the tank or its contents to a control interface for display of any and all desired data concerning the tank, its contents and/or conditions of the fluid within the tank, including, but not limited to temperature, density, carbon dioxide content, Brix (sugar content), pH, volume, time, geospatial information, tank identifier, fluid origin identifier, or the like.

DESCRIPTION OF THE FIGURES

The patent or application file contains at least one drawing executed in color. Copies of this patent or patent application publication with color drawing(s) will be provided by the Office upon request and payment of the necessary fee.

FIG. 6 is a temperature data map acquired from sensor arrays in a fermentation tank.

FIG. 7 is a temperature gradient map of interpolated data from sensor arrays in a fermentation tank.

DETAILED DESCRIPTION OF THE PREFERRED EMBODIMENTS

The present invention is described, by way of example, with reference to containment tanks that are wine fermentation tanks. Those skilled in the art will understand that any type of containment tank, whether for fluids, liquids, particulates, solids, semi-solids, suspensions or the like, in which it is desirable to monitor and/or control conditions within the tank, such as temperature, density, pressure or the like, is expressly intended to be within the scope of the present invention.

Figure 1:
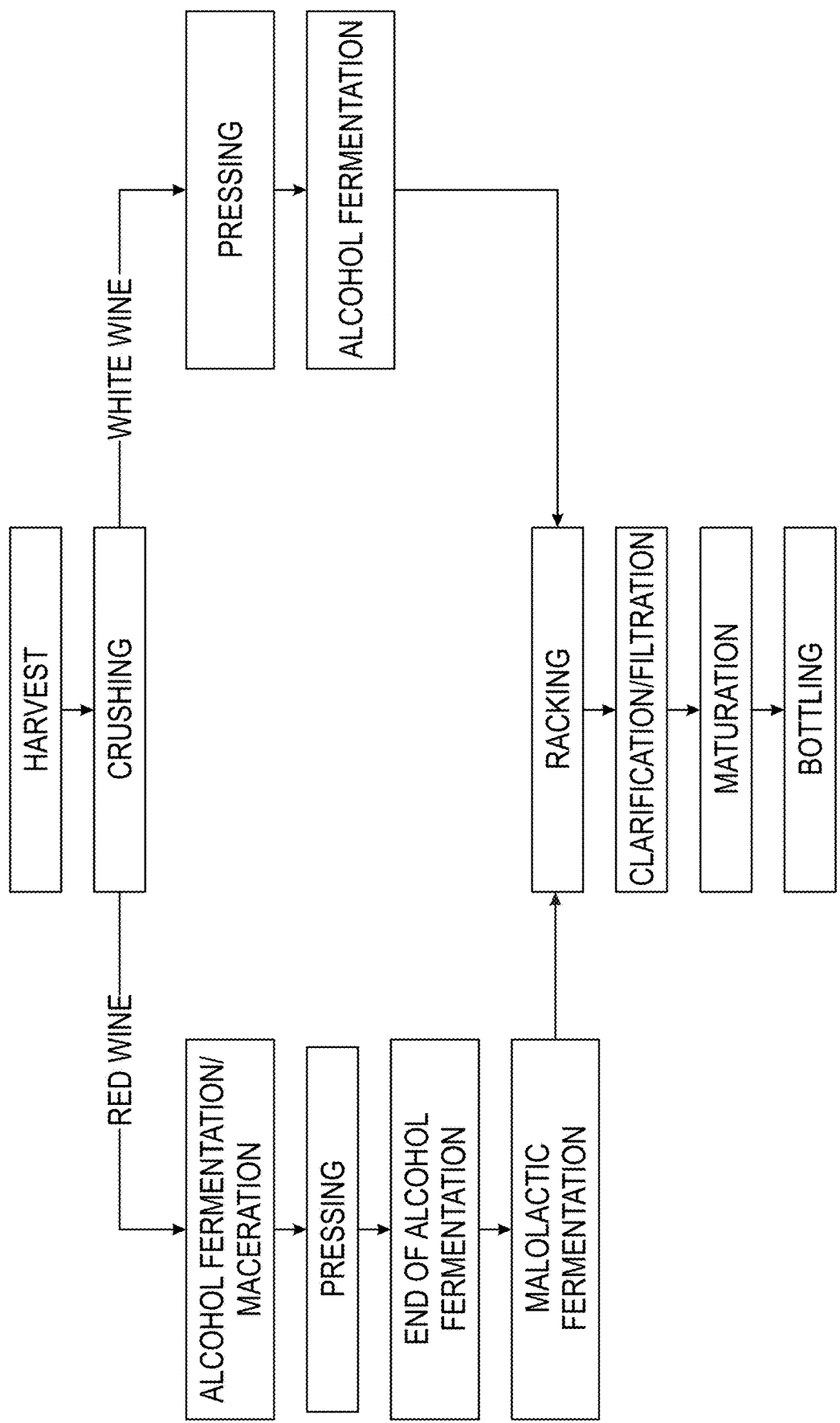
FIG. 1 is a flow chart illustrating the general process of wine making.

The process of wine making is illustrated in FIG. 1 and involves crushing large amounts of grapes into must, alcohol fermentation of the must in the presence of yeast under controlled conditions, pressing the fermented must to remove the solids, known as pomace in the wine making arts, and, in the case of red wines, fermenting malic acid to lactic acid in the presence of bacterial (malolactic fermentation) followed by racking, clarification and filtration maturation and bottling.

Figure 2:
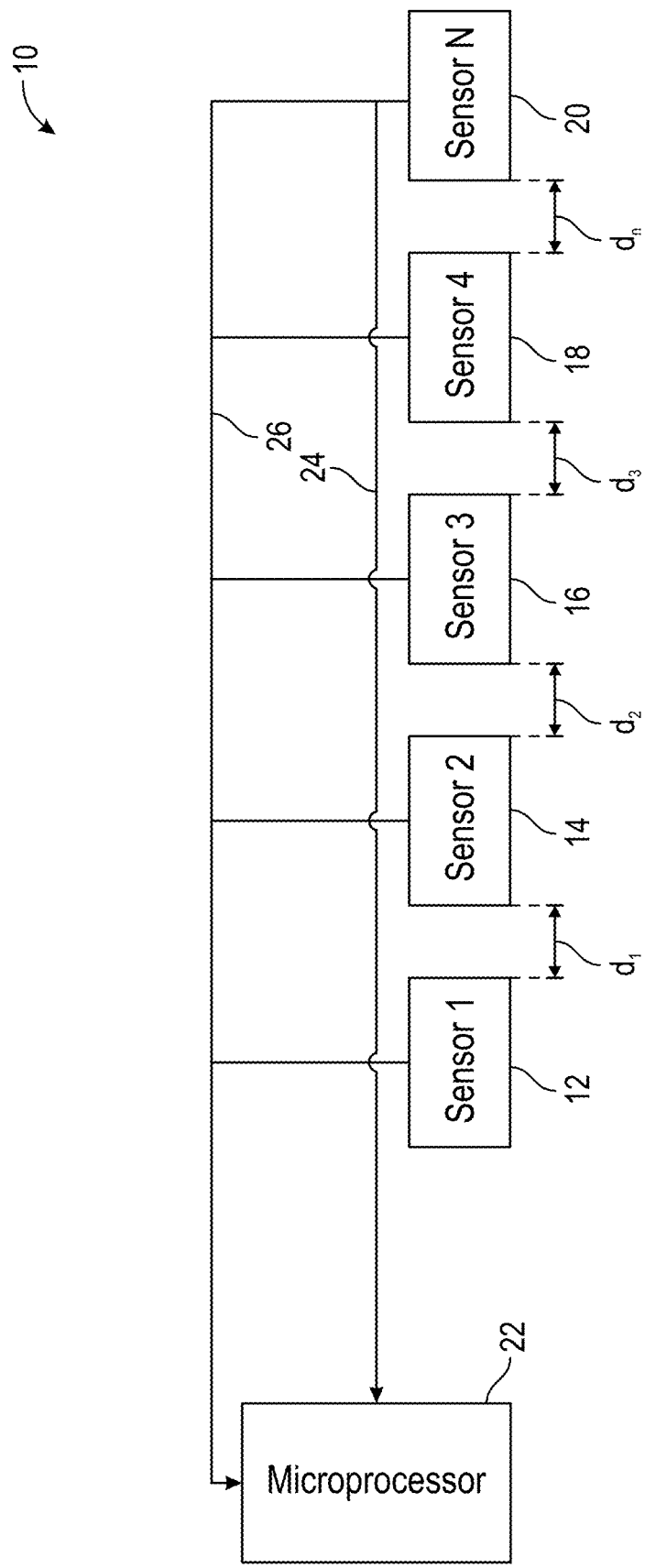
FIG. 2 is a schematic of a sensor array in accordance with the present invention.

The system and method of the present invention has general application in monitoring and controlling conditions of fluids, solids, suspensions, particulates or the like in a containment tank. By way of example only, the present invention has application in monitoring and controlling alcohol fermentation conditions in wine making. Those of ordinary skill in the art will understand that the system and method of the present invention is not intended to be limited to application in alcohol fermentation or wine making. Rather, the system and methods of the present invention are applicable to a wide range of containment vessels 42 where monitoring or controlling of environmental conditions with a containment vessel 42 are needed or are desirable. Examples of such other applications include, without limitation, oil and gas storage tanks, pipelines, transport vehicle containment tanks, grain storage silos and elevators, flour storage vessels, chemical storage or processing vessels, pharmaceutical or biological reaction or fermentation vessels, and/or alcohol fermentation, aging or storage vessels In order to create and facilitate the inventive system and method, very accurate data concerning conditions within the vessel 42 must be obtained from specific known locations within the vessel 42. The known locations are related to the geometry of the vessel 42. In most cases a multi-point sensor, synonymously referred to as a sensor array 10, is positioned at the center axis of the vessel 42 and another sensor array is positioned proximate an inner wall surface of the vessel 42. Each sensor array has a plurality of sensors positioned in spaced apart fashion along a longitudinal axis of the sensor array. Each of the plurality of sensors 12, 14, 16, 18, 20 are spaced a known and predefined distance from adjacent sensors and the inter-sensor spacing is the same between sensor arrays 10. An example of a sensor array is depicted in FIG. 2 in which a plurality of sensors, such as temperature sensors, are longitudinally arrayed and electrically coupled 24, 26 to a microprocessor 22. Each of the plurality of sensors in each of the sensor arrays are spaced apart from each other a predetermined and known distance $d_1, d_2, d_3 \ldots d_n$. The known distances $d_1, d_2, d_3 \ldots d_n$ may be different from one another such that $d_1 \neq d_2 \neq d_3 \neq d_n$ or may be equal such that $d_1 = d_2 = d_3 = d_1$. Alternatively, one of the known distances may be different from the others, for example $d_1 = d_2 = d_3 \geq d_n$. The know distances help to form coordinates or map out sensor positions relative to the walls of the storage vessel 42. Additionally, each of the sensor arrays 10, that is a first sensor array at the vessel center and a second sensor array at the tank's inner periphery are positioned such that sensor 1 12 in the first sensor array is vertically aligned with sensor 1 12 in the second sensor array, sensor 2 14 in the first sensor array is vertically aligned with sensor 2 14 in the second sensor array, and so on, ensuring each of the individual sensors are vertically aligned along a vertical axis of the tank 42 between the first sensor array 10 and the second sensor array 10.

The plurality of sensors in each of the first and second sensor arrays are electrically coupled to a microprocessor 22 that acquires signals from each of the sensors in the sensor array 10 and outputs digital data corresponding to the condition being sensed by each of the sensors. In accordance with one aspect of the invention, each of the plurality of sensors are temperature sensors. In accordance with another aspect of the invention, one or more of the plurality of sensors in a sensor array are selected from the group of sensors for flow, density, pressure, pH, Brix, carbon dioxide, or other chemical property or physical property.

As the system and method of the present invention is agnostic to vessel geometry, the vessel may be of any configuration known in the art, including cylindrical, cubic, tubular or other shaped vessel. The regression model may be adjusted to the match the dimensional confines of the vessel geometry. In some cases, the use of a multi-point sensor could be placed in the center of the vessel in any orientation as long as parallel or non-parallel measurements are taken elsewhere. Those skilled in the art will appreciate that where more known points from sensor data measurement are acquired, less interpolation is required. The inventive interpolation model allows for known data values to be supplemented with other sensor data obtained from any other region within the vessel.

Fermentation tanks 42, such as those employed in winemaking or beer making, are typically large, generally vertically oriented, stainless steel tanks. As alcohol fermentation is an exothermic process, the fluid within the tank 42 is subjected to temperature excursions that vary within the mass of fluid in the tank 42. It is customary to employ jacketing around the fermentation tank to circulate a thermal fluid, such as glycol, to control the temperature excursions and maintain the bulk of the fluid within the fermentation tank within acceptable temperature norms.

Containment tanks 42 are typically vertically oriented tanks with a large fluid chamber bounded by the tank. Wine fermentation tanks 42 are often cylindrical and have an upper lid opening to introduce material, such as fluids, solids or particulates, such as must, produced from freshly crushed grapes in winemaking, and a lower valve or other openings to allow for withdrawal of fluid and particulates from the tank 42.

Figure 3:
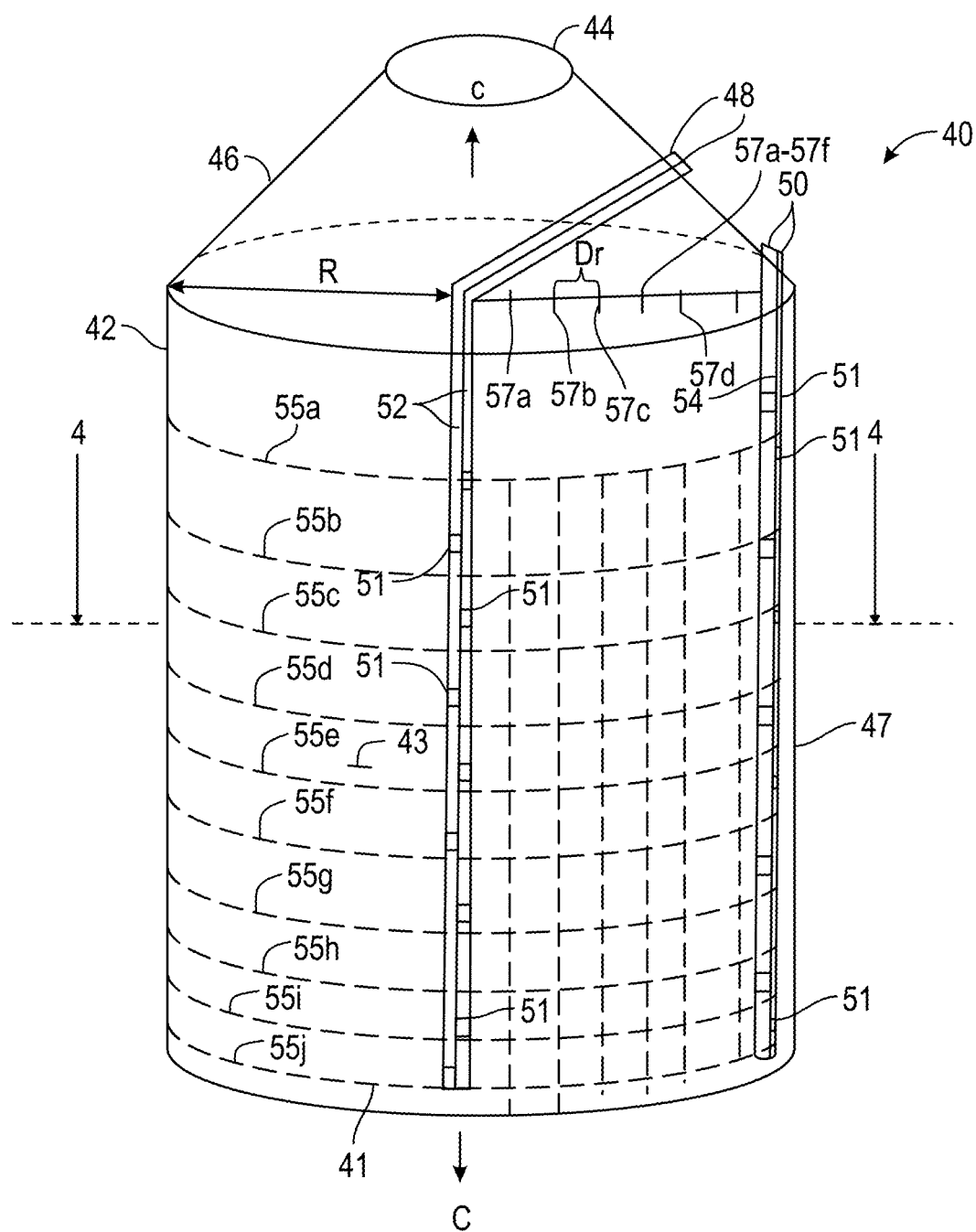
FIG. 3 is diagrammatic perspective view of a tank having two sensor arrays contained within the tank.
Figure 4:
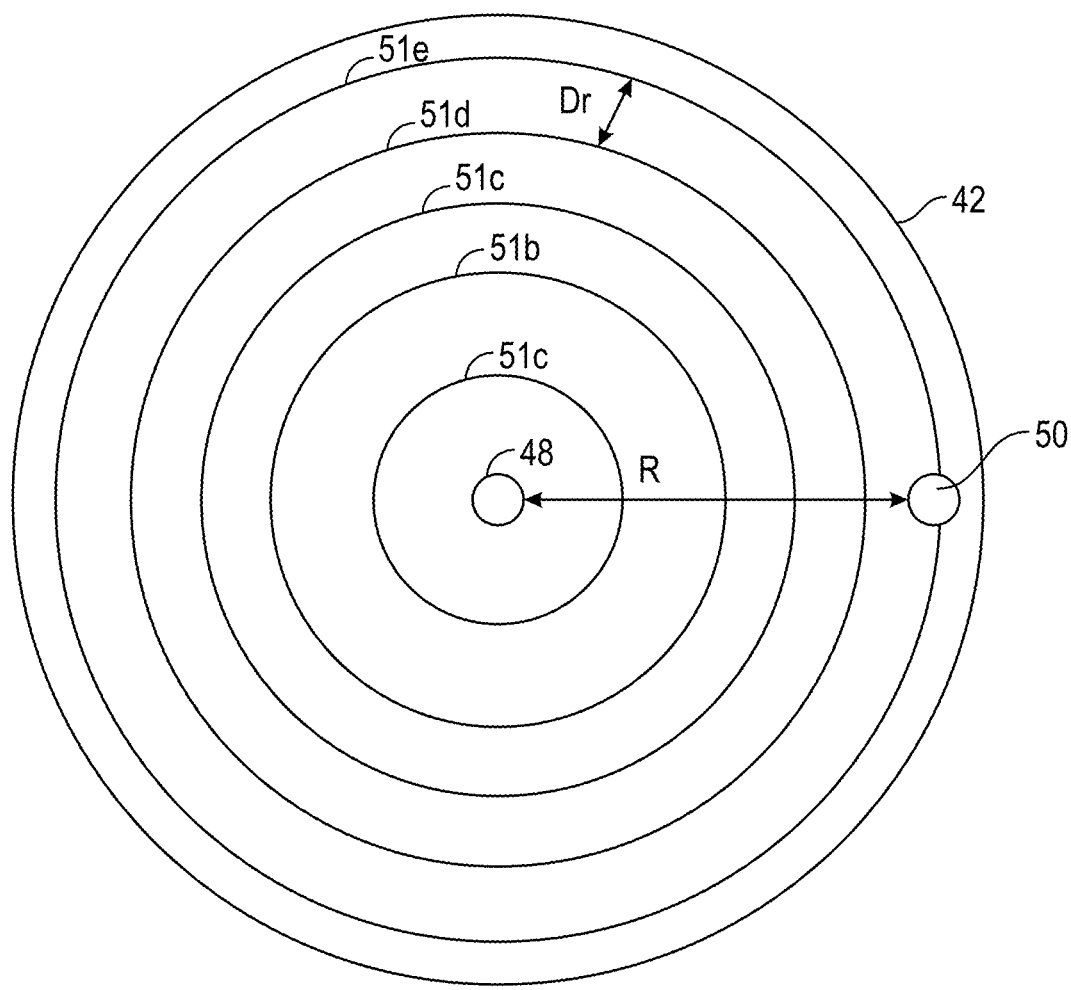
FIG. 4 is a cross-sectional diagrammatic view taken along line 4-4 of FIG. 3.

FIGS. 3 and 4 depict an exemplary system 40 with a cylindrical tank 42 having a longitudinal central axis C, an upper opening 44 into which substances, such as, for example, crushed grapes or must are introduced. At least two thermowells 48, 50 are positioned in the tank 42 to facilitate introduction of sensor arrays 52, 54 into the tank. As noted above, a thermowell 48, 50 is a tubular jacket that is positioned in the fluid chamber 43 of the tank and sealed so that fluid within the fluid chamber does not penetrate into the thermowell 48, 50. The sensor arrays 52, 54 are each placed within the thermowell tubular jackets 48, 50 so that they are protected by the tubular jacket from the fluid within the tank 42 and are operatively coupled to the particular condition within the tank, such as temperature, pressure, density, being sensed. The tubular jacket of the thermowell 48, 50, therefore, communicates the property or properties being sensed by the sensor array from the tank 42, through the tubular jacket to the sensor within the thermowell 48, 50. Each thermowell extends from an upper surface 46 of the tank 42 where the thermowell is capable of being opened to introduce the sensor array 52, 54 into the tubular jacket of the thermowell 48, 50 to a position proximate or at an inner bottom surface 45 of the fluid chamber 43 of the tank 42.

Since fermentation tanks 42 typically have thermal jacketing about their inner or outer periphery, it is preferable to avoid positioning the thermowells 48, 50, such that their entry points into the tank 42 penetrates into the thermal jacketing. It has been found advantageous to employ a first thermowell 48 positioned centrally within the tank 42, i.e., extending vertically along the central axis C of the tank 42 and having a radius bend such that passes through a top surface 46 of the tank 42 offset from the center of the top surface 46. A second thermowell 50 is positioned radially offset R from the first thermowell 48 and proximate to an inner edge 47 of the fluid chamber 43 and extending vertically into the fluid chamber 43 and parallel to both the inner edge 47 of the fluid chamber 43 and the first thermowell 48. The second thermowell 50 may be positioned at any desirable position in the tank 42 and spaced a known distance D from the first thermowell 48. It is preferable that the second thermowell 50 projects directly through the top surface 48 of the tank without a bend such that it does not penetrate the thermal jacket.

At least one sensor array 52, 54 is placed into each of the first and second thermowells 48, 50. As discussed above, each sensor array 52, 54 has a plurality of sensors positioned at known spaced apart distances $d_1, d_2, d_3 \ldots d_n$. Similarly, the radial distance R between the first thermowell 48 and the second thermowell 50 may be segmented into plural known units $D_r$ defining longitude lines 57a, 57b, 57c, 57d, 57e 57f. FIG. 4 shows a cross-section of the tank 42 showing these extrapolated distances 57a, 57b, 57c, 57d, 57e 57f. In this manner, aligned pairs of the plurality of sensors 51 in the first sensor array 52 and in the second sensor array 54 define latitude lines 55a, 55b, 55c, 55d, 55e, 55f, 55g, 55h, 55i, 55j extending transverse to the central axis C of the tank 42 and extending between the first sensor array 52 and the second sensor array or the inner surface 47. These latitude lines 55a, 55b, 55c, 55d, 55e, 55f, 55g, 55h, 55i, 55j are extrapolated about the entire circumference of the tank 42. Similar to the latitude lines, the longitude lines 57a, 57b, 57c, 57d, 57e 57f extend parallel to the central axis C of the tank 42, parallel to the first sensor array 52 and second sensor array 54, and extend between the first sensor array 52 and the second sensor array 54 or the inner surface 47 of the tank 42. The longitude lines are also extrapolated about the entire inner circumference of the tank 42. The extrapolation of the longitude lines between co-planar sensors in the first sensor array 52 and the second sensor array 54 when combined with the extrapolation of the latitude lines parallel to the central axis C of the tank and the first sensor array 52 and second sensor array 54, form a grid pattern within the volume of the tank from which the known data from the sensors may be interpolated and a three dimensional regression analysis on the data may be performed.

A suitable sensor array is described in U.S. Pat. No. 7,004,624, which is hereby incorporated by reference and referred to as "the '624 Patent." As described in the '624 patent a thermal sensor probe includes a plurality of digital temperature sensors housed in a thermally conductive housing. The probe includes a bus connected to each of the plurality of digital temperature sensors and a controller coupled to each sensor via the bus which collects temperature data from each of the sensors. In accordance with the present invention, the temperature sensors linearly arrayed along a common bus backbone and are in thermal contact with an inner wall surface of the thermowell. The thermowell is thermally conductive and communicates the temperature of the fluid contacting an outer surface of the thermowell to each of the temperature sensors.

Those skilled in the art will understand that other types of digital and/or analog sensors, including without limitation, for example, density sensors, Brix sensors, flow sensors, volume sensors, carbon dioxide sensors, pH sensors, or the like, which are suitable for different conditions to be monitored and/or controlled within the containment vessel, may also be incorporated into the sensor array or may be incorporated into the system in separate thermowells, in known positions along the sensor arrays and within the tank. In this manner, the data from the other digital and/or analog sensors may be acquired, interpolated and displayed in a manner similar to the data from the temperature probes. For example, in one aspect of the present invention, a fork density sensor (Micro Motion, Inc. Boulder, Colorado, distributed by Emerson Automation, such as that described in U.S. Patent Application Publication No. US2016/0109345, which is hereby incorporated by reference in its entirety) is positioned passing through a side wall of the tank and proximate the bottom inner surface of the tank in a lower portion of the tank where solids collect. In accordance with the present invention, data from the density sensor may be used to derive Brix values or, alternatively, a Brix sensor is positioned proximate the density sensor and in proximity to an output valve on the tank. A screen is employed to cover the density sensor, the Brix sensor, if present, and the output valve. The screen has an opening size sufficient to allow for fluid flow through the screen but to exclude solids which risk confusing the sensors and providing inaccurate data. Moreover, the screen allows for fluid flow into and through the output valve and allows for accurate readings of density and Brix in the fluid during pump overs.

Interpolation Model

Figure 5A:
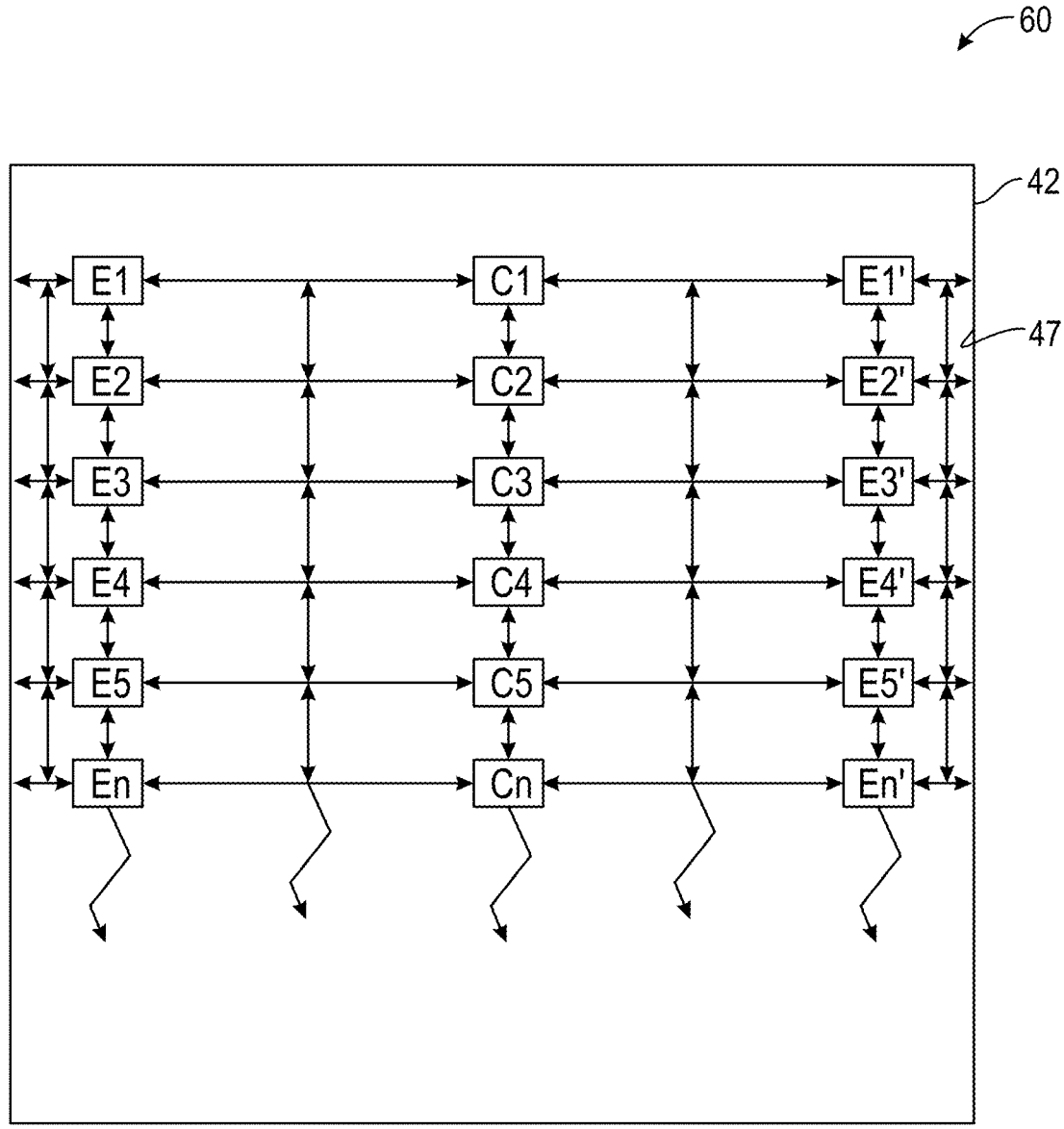
FIG. 5A is a regression map illustrating sensor array interpolation along plural axes of the tank.
Figure 5B:
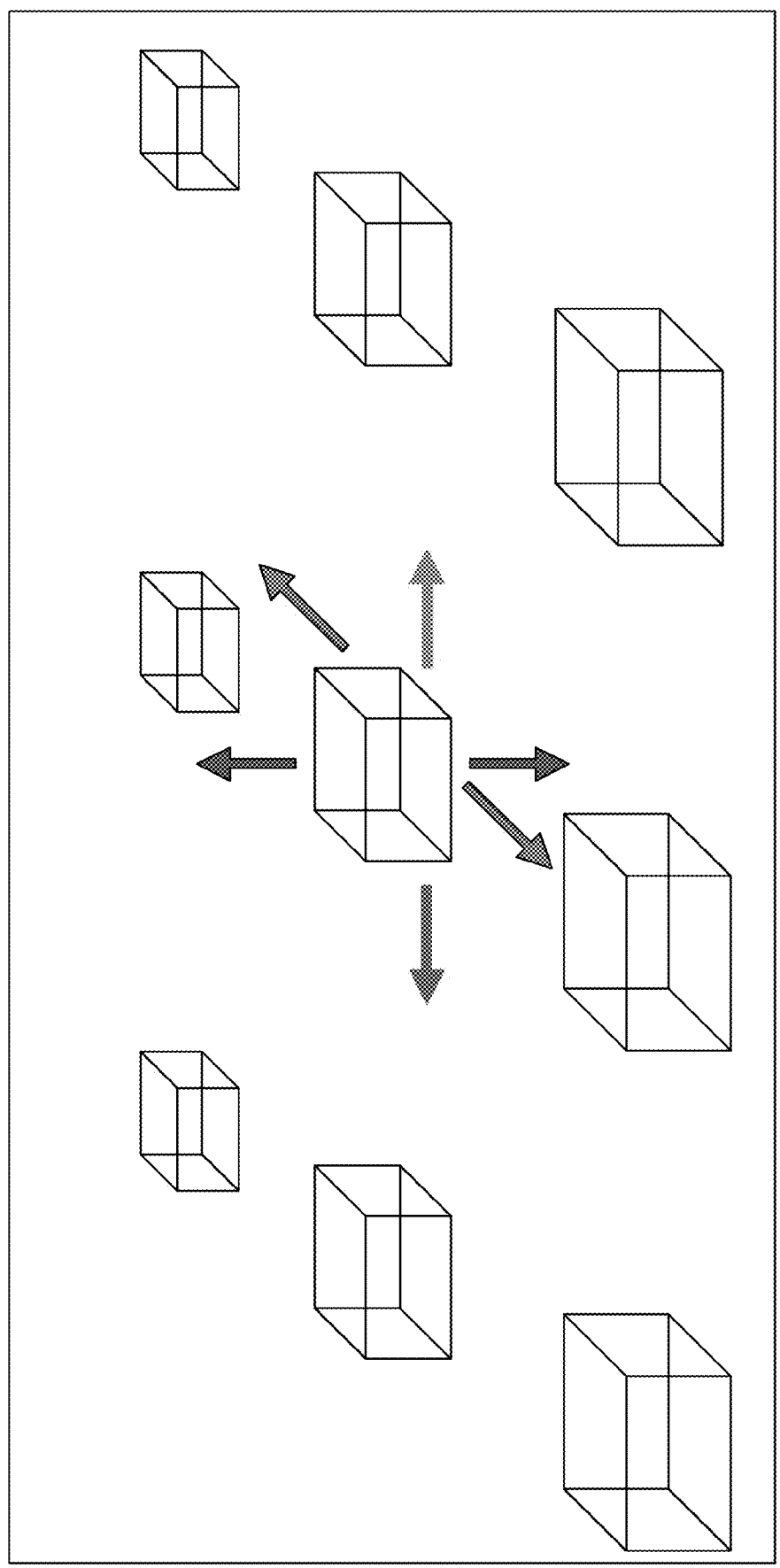
FIG. 5B is a diagrammatic example of tri-cubic interpolation along three axes of a three-dimensional space.

The interpolation model uses the series of three-dimensional data points from the sensors and interpolates data points from the known sensor data into the three-dimensional space bounded by the known data points. From this interpolated data, regression modeling is applied to identify data relationships and trends. The interpolation schema 60 in tank 42 is represented in FIG. 5A. E1 to En are the known sensor data points arranged in their known spatial positions from the second sensor array 52 positioned proximate the inner tank surface 47. C1 to Cn are the known sensor data points arranged in their known spatial positions from the first sensor array 54 positioned at the central axis C of the tank 42. Sensor data points E1' to En' are estimated data points based upon the assumption that the data at the diametrically opposite position adjacent the inner tank wall from the second sensor array 52, i.e., diametrically opposite sensor data points E1 to En, are the same. The arrows extending laterally between E1, C1 and C1 and E1', as well as the lateral arrows extending between E1' and the tank wall 47 and D1 and the tank wall 47, and their corresponding lateral arrows down the vertical axis of the tank 42 define the interpolation relationships along the latitude lines 55a to 55g in FIG. 3. Similarly, the vertical arrows extending between E1 and E2, C1 and C2, E1' and E2', as well as the other vertical arrows arranged about the horizontal axis of the tank 42 define the interpolation relationships along the longitude lines 57a to 57e of FIG. 3. FIG. 5B illustrates the principal of tri-cubic interpolation along three axes of a three-dimensional space, such as a containment vessel. In this manner, the inner volume of the tank is defined as a three-dimensional grid and the known data points are interpolated along both the latitude lines and the longitude lines to fill in the spatially separate grid points of unknown data across the tank's inner volume.

The known and interpolated data values are then laid into a 2D matrix or table to represent geometric properties of the containment vessel along any desired longitudinal or latitudinal slice through the tank 42. FIG. 6 is a 2D matrix or Table 1 100 of temperature data interpolation from nine sensors in each of the first sensor array 52 and the second sensor array 54. This data was processed using three-dimensional cubic interpolation. The X and Y axis 102, 104 of Table 1 represent the lateral and longitudinal coordinates of the interpolated slice, while the exemplary data cell 106 represents a measured sensor value (or temperature value in this embodiment)

Figure 8:
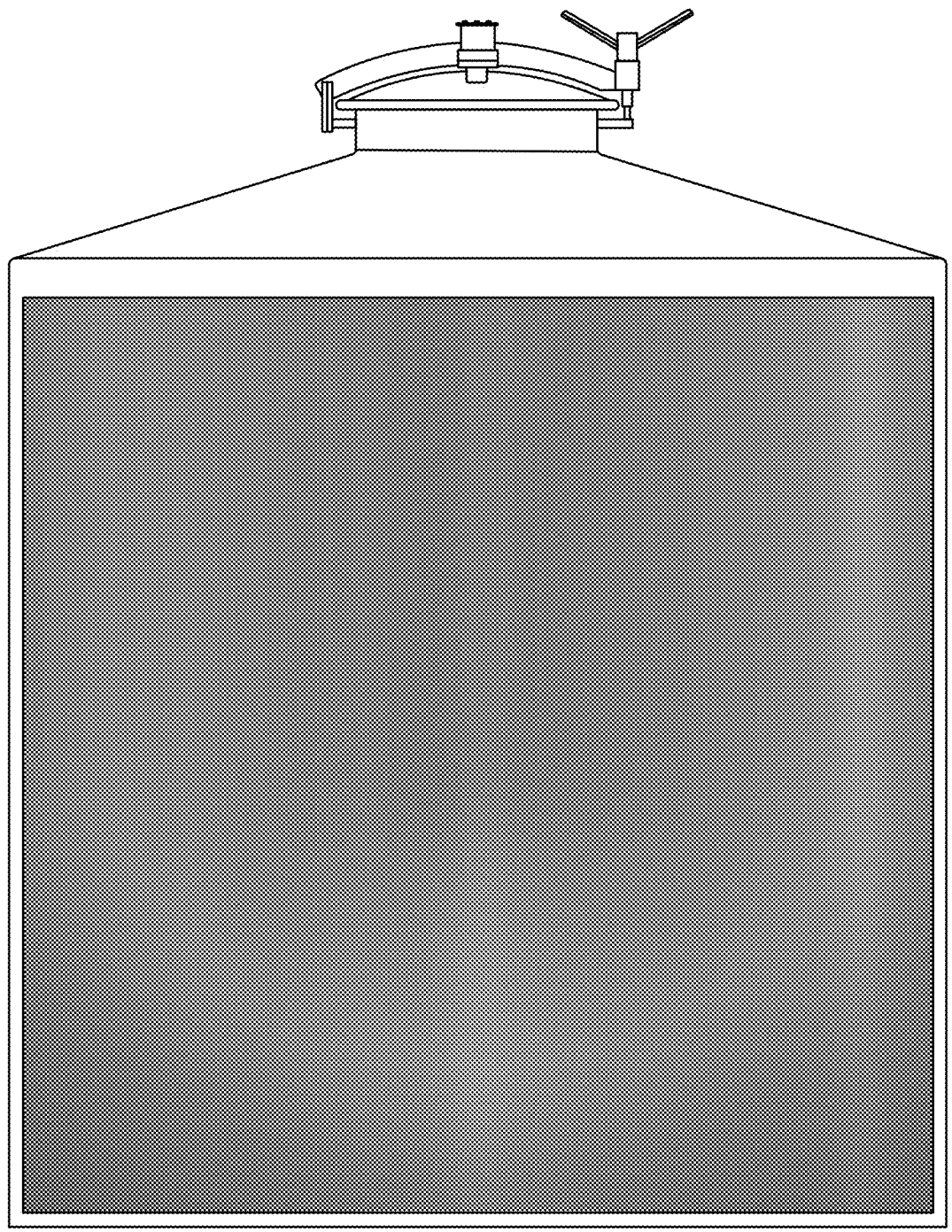
FIG. 8 is a graphical display of the temperature gradients overlaid onto a schematic of a tank.

The interpolated data values from FIG. 6 were then assigned HSB (hue, saturation, brightness) color values and these values were then used to generate a gradated color temperature interpolation table reflecting the interpolated temperature gradients within the vessel as shown in Table 2 200 of FIG. 7. The X and Y axis 202, 204 of Table 2 represent the lateral and longitudinal coordinates of the interpolated slice, while the exemplary data cell 206 represents a measured sensor value (or temperature value in this embodiment). As shown in FIG. 7 by way of example, colder temperatures take on a darker purple hue 208 while the warmest areas are mapped with a brighter red/orange color 210. FIG. 8 is a simulated output of an interpolated thermal state within a wine fermentation vessel 42 representing the ranges of thermal values based upon position within the vessel taking data from a gradated color temperature interpolation table, such as that shown in FIG. 7.

It will be appreciated by one skilled in the art, that by positioning the plurality of sensors to define axes within the tank, the area within the tank is effectively divided into a three-dimensional grid. This three-dimensional regular grid then allows for application of known three-dimension interpolation techniques to interpolate condition values, for example temperature or density values, across the three dimensional grid based upon the known data points. In a cylindrical vessel with two parallel or non-parallel multi-point temperature sensors (center and edge) the results are assumed to be radially congruent and the edge multi-point sensor data is replicated for the diametrically opposite edge of the vessel. Alternatively, additional multi-point sensors may be placed in thermowells in different positions within the vessel, relative to the first and second thermowells, in order to generate actual data across other spatial points about the longitudinal or latitude lines within the vessel or to create additional axes corresponding to different sensor positions. The interpolation model of the present invention will operate on known data points anywhere within the vessel.

Known methods of three dimensional interpolation are exemplified by Lekien, F., et al., Tricubic interpolation in three dimensions, Int. J. Numer. Meth. Engng., 2005; 63:455-471, incorporated herein by reference, describe a local tricubic interpolation scheme in three dimensions. Alternatively, trilinear interpolation is a method of multivariate interpolation on a 3-dimensional regular grid and may be used to interpolate sensor data across the area of the interior chamber of the tank.

As the thermal state of the fluid within a containment tank, particularly a fermentation tank, is constantly changing, the interpolation model will preferably run dynamically or constantly and generate a dynamically updated image of the conditions within the containment vessel. For example, during what is known as a "pump over", relatively colder fluid that collects at the bottom of the tank is pumped from the bottom of the tank to the top of the tank where there is relatively warmer fluid. The thermal effects of this pump over mixing may be closely monitored in real time using the image generated from the interpolation model of the present invention and guide the user in evaluating the duration and effectiveness of the pump over to the overall temperature profile of the fluid mass in the vessel. Another example is monitoring the thermal and density effects of yeast inoculation into the fluid within the vessel. The exothermic reaction of the yeast with sugars in the fluid may be monitored in real time and the temperature profile may be monitored and controlled within defined parameters based upon the monitoring of the interpolation model data. Further, carbon dioxide released during the fermentation process will affect the density of the fluid within the vessel and the density variances and gradients may be monitored and controlled by adjusting the temperature within the vessel and, therefore, the kinetics of the fermentation reaction.

Response Logic

As noted above, fermentation vessels, such as those used in wine making, typically employ one or more thermal jackets through which a thermal fluid, such as glycol, is recirculated from a heat exchanger through the thermal jackets. The thermal fluid flow through the one or more thermal jackets may be operated automatically in response to a logic control circuit with input from the plurality of sensors or may be operated manually or both. The logic control circuit is electrically coupled to a plurality of valves that control flow of thermal fluid into and out of the one or more thermal jackets in response to the data signals from the plurality of sensor arrays.

Where there is more than one thermal jacket, each thermal jacket may operate independently of other thermal jackets to heat or cool the individual thermal jackets independent of one another. In wine making, for example, the thermal gradients within the fermentation tank tend to be controllable within well-defined ranges. Thus, typically one or more thermal jackets may be cooled simultaneously, at the same or different cooling rates, or the one or more thermal jackets may be heated simultaneously, at the same or different heating rates, or the one or more thermal jackets may be independently cooled or heated without cooling or heating other thermal jackets. Typically, however, where there is a plurality of thermal jackets on a fermentation tank, simultaneous heating and cooling is not preferred.

Control Interface

Figure 9:
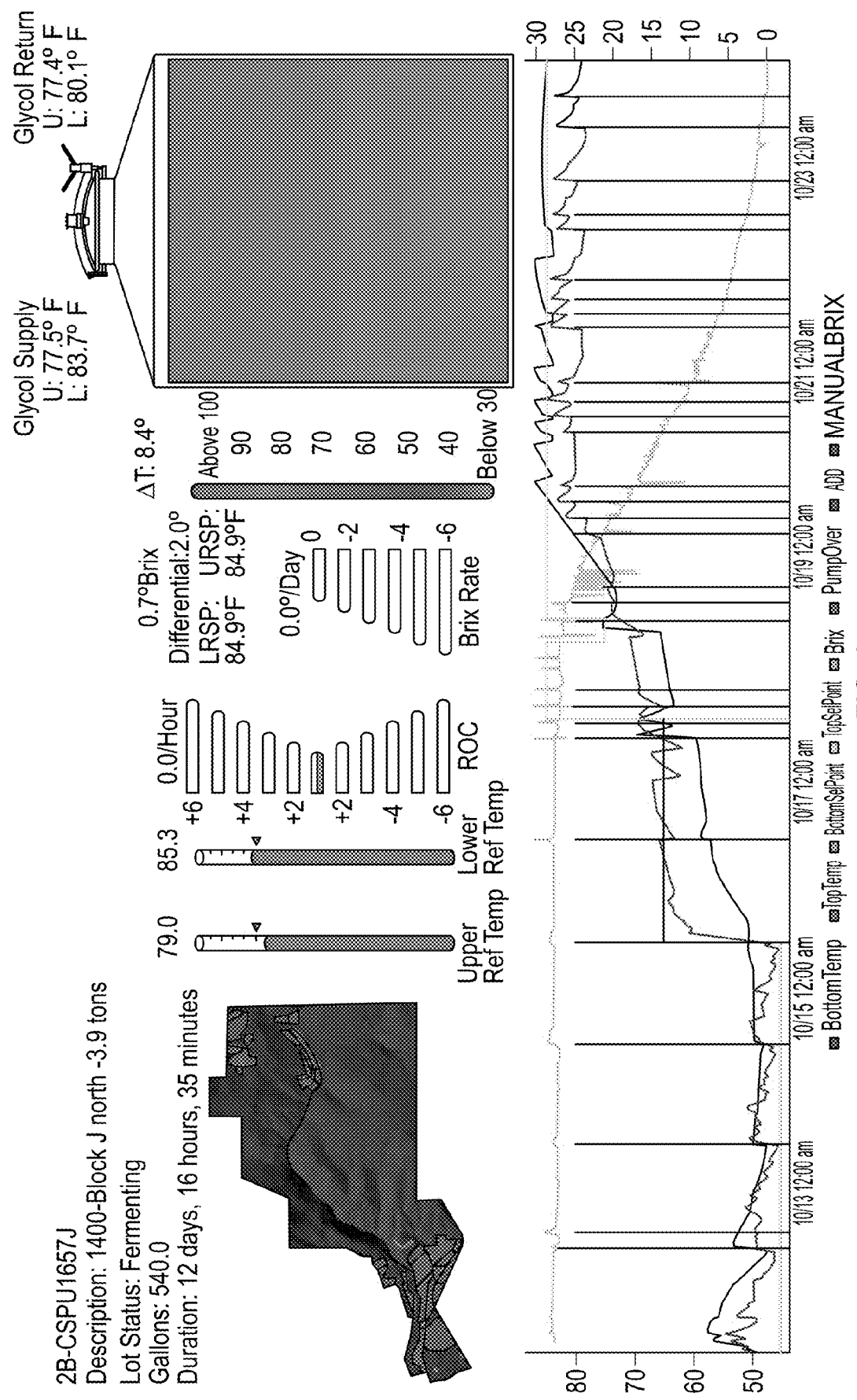
FIG. 9 is an exemplary control screen graphical user interface display in accordance with the present invention.

The plurality of sensors output data signals corresponding to the conditions being sensed, monitored and/or controlled within the tank. Analog signals are converted to digital signals and all data signals are communicated to a network server, which may be a local area network server or a cloud server. The data signals from the sensor arrays are processed at the server and may be combined with other data at the server, such as geospatial data, batch identifier data, tank identifier data, thermal jacket temperature data, time data, activity data, chemical data, ambient environmental data, trend data or any such other data as is desirable to visualize and correlate with the data from the plurality of sensors on a graphical display or displays. Control screens employ series of derived data to create a display visualization on the control screen and provide a graphical user interface that allows a user to interact with various data and data sources displayed on the control screen. FIG. 9 depicts an exemplary control screen and graphical user interface 300 in accordance with the present invention.

Data relevant to each container and its contents is stored in one or more databases accessible by the server. In this manner, process data related to the current batch processing may be compared against historical data for similar conditions within the tank, identify what processes were employed under such similar conditions and, thereby, allow for modeling of conditions and their response to various controls over time. Moreover, the historical data preferably contains identifying information about the contents of the tank. Such content identifying information may include, for example, geospatial data identifying the origin of the container contents, e.g., field, lot, row, GPS coordinates, etc., date, time or environmental condition data, for example, the harvest date and time, the crush date and time, environmental conditions existing on the harvest date or crush date, environmental conditions for the growing season, soil conditions, or the like. All of the data stored in the one or more databases is accessible for use displaying on the control screens and in modeling the conditions within the tank and most desirable control parameters for such conditions.

FIG. 9 is a screen capture of a graphical display of data representing conditions within a particular alcohol fermentation tank, for a particular harvest batch, from a particular portion of a vineyard, taken at a particular moment in time. As is illustrated in FIG. 9, a wide variety of data may be displayed and monitored over a time scale to create a dynamic view over time of the conditions within the tank and their responsiveness to controls or interventions, such as a pump over. As depicted in FIG. 9, this is a representation of the state within the fermentation tank depicted graphically in the upper right of the Figure, of a batch resulting from a crush of 3.9 tons of grapes harvested from Section 1400, Block J North of a vineyard, depicted graphically in the upper left hand section of the Figure. The fermentation tank has 540 gallons of must fermenting in the tank for 12 days, 16 hours and 35 minutes. The display also provides information about the upper and lower temperature ranges within the tank and the Brix value. A time scale is depicted along the lower horizontal axis of FIG. 9 and tracks changes in conditions within the tank as well as controls and interventions, such as manual Brix measurements, automatic Brix measurements, pump overs, and temperature excursions over time.

It will be appreciated by those skilled in the art that the data acquired and interpolated by the present system and method, together with regression modeling of that data, serves as a strong basis for machine learning or artificial intelligence applied to monitoring and control wine fermentation processes or other processes in which control over conditions within a containment vessel are required. Virtually any type of repetitive processing where material is either processed or stored in containment vessels will benefit from the system and method of the present invention. The machine learning or artificial intelligence aspect of the present invention allows for consistently better monitoring and tighter control over the repetitive processes within a containment tank. Additionally, because the system and method of the present invention provide a large amount of data continuously over a period of time in a three-dimensional environment, augmented reality applications are well-suited to use with the present invention. For example, the visual interface used in many augmented reality applications is worn on a user's head and three-dimensional images are displayed in the visual interface and may be manipulated either by the user moving her head, eyes, hands, fingers or her body position. In this manner, augmented reality interfaces will allow for three-dimensional visualization with a containment vessel of the state of conditions within any spatial position within the containment vessel. Access to this level of spatial information will allow the user a level of monitoring at the level of the three-dimensional unit defined by the interpolation model, i.e., the smaller the three-dimensional unit, e.g., a cubic unit, the finer resolution the user will have over monitoring conditions with the containment vessel. Similarly, with finer resolution, the user will have a correspondingly greater level of control to allow for either automatic interventions or manual interventions.

Alternative Applications

The benefits of understanding the thermal state of a vessel are not limited to the wine industry. The concept can be applied to any environment where complex inhomogeneous or homogeneous thermal environments need to be controlled or studied. This would work both with a mixing environment where controlled homogeneity is trying to be accomplished and verified. Similarly, it would be beneficial with a vessel where no mixing occurs and a thermally inhomogeneous environment requires understanding. Any application that undergoes a biological reaction, such as in pharmaceuticals, temperature control and its understanding is critical. Chemical processing where exothermic reactions occur in vessels could be more closely monitored. Cooling and heating elements on vessels could be more tightly governed as temperature conductance and convection is visualized. Also, the process can be applied to any medium at any density. Liquid, solid, gaseous states or even a mixture of these in a vessel would still benefit from this technology. The method of measurement and form of regression model can change for optimization regardless of the product being thermally interpolated.

While the invention has been described with reference to its exemplary embodiments, those skilled in the art will understand and appreciate that the regression model described in the present invention is not limited to the specific examples provided herein. Rather, the scope of the present invention is intended to be construed only with reference to the appended claims.

What is claimed is:

1. A system for monitoring and controlling conditions within a fluid containment vessel, comprising:
   a. at least two of a plurality of sensor arrays, each of the plurality of sensor arrays having a length configured to allow each sensor array to extend between an inner bottom surface and an inner top surface of the fluid containment vessel; each of the plurality of sensor arrays having a plurality of sensors spaced along the length of the sensor array that are positioned within a housing that isolates each sensor array from fluid within the fluid containment vessel, each of the plurality of sensors configured to sense a condition to be monitored or controlled within the fluid containment vessel;
   b. the at least two of a plurality of sensor arrays being positioned within the fluid containment vessel such that each of the plurality of sensors are in vertical alignment between the at least two of a plurality of sensor arrays;
   c. a computer in communication with each of the plurality of sensors which receives signals from each of the plurality of sensors corresponding to at least one condition sensed by each of the plurality of sensors within the fluid containment vessel; and
   d. a processor configured to process the signals received from each of the plurality of sensors, assign known sensor data points associated with each of the plurality of sensors, generate estimated sensor data points, each estimated sensor data point being spatially separate from each known sensor data point from the first of the plurality of sensor arrays and the second of the plurality of sensor arrays in the fluid containment vessel, and interpolate the signals across a majority of volume within the fluid containment vessel between the known sensor data points and the estimated sensor data points.

2. The system according to claim 1, wherein the at least two of a plurality of sensor arrays further comprise a first sensor array and a second sensor array, and the first sensor array is positioned proximate to a center of the fluid containment vessel and the second sensor array is positioned proximate to a side wall of the fluid containment vessel.

3. The system according to claim 1, further comprising a first housing passing into the fluid containment vessel and positioned along a central axis of the fluid containment vessel and a second housing passing into the fluid containment vessel and positioned proximate to a side wall of the fluid containment vessel, at least one of the plurality of sensor arrays being disposed in the first housing and second housing.

4. The system according to claim 2, wherein at least one of the plurality of sensor arrays further comprises temperature sensor arrays.

5. The system according to claim 4, wherein a temperature sensor in the temperature sensor arrays is selected from the following: thermometer, thermocouple, thermistor, or resistance temperature detector.

6. The system according to claim 2, wherein the sensors within the sensor arrays are selected from flow, density, pressure, pH, Brix, carbon dioxide, or other chemical property or physical property.

7. The system according to claim 1, further comprising a three-dimensional cubic grid defined by the processor along latitude and longitude axes within the fluid containment vessel and between the known data points and the estimated data points.

8. The system according to claim 7, wherein the computer and processor are configured to conduct regression analysis of and interpolate data from the known data points and estimated data points throughout the three-dimensional grid.

9. The system according to claim 8, further comprising a display in communication with the computer, the display being capable of displaying interpolated data from either or both latitude or longitude axes.

10. The system according to claim 9, further comprising a controller in communication with the computer and at least one of a plurality of valves and a plurality of pumps.

11. A method for monitoring and controlling conditions within a fluid containment vessel, comprising the steps of:
   a. Positioning at least two sensor arrays within a fluid containment vessel such that each sensor in a first of the at least two sensor arrays is in vertical alignment a sensor in a second of the at least two sensor arrays;
   b. Sensing a condition within the fluid containment vessel at a plurality of spatially separate positions within the fluid containment vessel and outputting known sensor data from each of the first sensor array and the second sensor array;
   c. Generating estimated sensor data from positions spaced apart from each known sensor data point from the second of the at least two sensor arrays in the fluid containment vessel;
   d. Conducting regression analysis on the known sensor data and the estimated sensor data and interpolating known sensor data and the estimated data sensor across at least a majority of the fluid containment vessel's internal volume; and
   e. Mapping the interpolated data to represent a distribution of interpolated data across the volume of the fluid containment vessel.

12. The method of claim 11, further comprising the step of color coding the mapped interpolated data and displaying hue, saturation, brightness color values corresponding to gradients in the values of the interpolated data from the known sensor data and the estimated sensor data.

13. The method of claim 11, wherein the step of sensing a condition within the fluid containment vessel further comprises the step of sending temperature at a plurality of spatially separate positions within the fluid containment vessel.

14. The method of claim 11, further comprising the step of defining a three-dimensional grid prior to the step of interpolating data.

15. The method of claim 14, wherein the step of interpolating data further comprises three-dimensional cubic interpolation.

16. The method of claim 14, wherein the step of interpolating data further comprises the step of tri-linear interpolation.

17. A method for monitoring and controlling temperature of a fluid within a fluid containment vessel, comprising the steps of:
   a. Sensing a known value of a temperature condition of the fluid within the fluid containment vessel at a first position and estimating an estimated value of a temperature condition at a second position spatially distinct the first position of the known value;
   b. Determining at least one positional coordinate of the known value and the estimated value of the temperature conditions within the fluid containment vessel;
   c. Comparing the known value and the estimated value with a predetermined value for each positional coordinate corresponding to the known value and the estimated value;
   d. Determining if each value of the sensed temperature condition meets or exceeds the predetermined value; and
   e. If the value of the sensed temperature condition exceeds the predetermined value, circulating a thermal fluid within a thermal jacket coupled to the fluid containment vessel for a period of time sufficient to decrease the value of the sensed temperature condition to within the predetermined value.

18. The method of claim 17, wherein the temperature condition is sensed with a sensor further comprises a thermocouple, thermistor, thermometer, or resistance temperature detector.

19. The method of claim 17 wherein the step of circulating a thermal fluid further comprises the step of actuating a pump.

20. The method of claim 19, further comprising the step of circulating the thermal fluid through a heat exchanger.

* * * * *